(12) United States Patent
Webster et al.

(10) Patent No.: US 8,017,795 B2
(45) Date of Patent: Sep. 13, 2011

(54) RADIATION CURABLE POLYMER FILMS HAVING IMPROVED LASER ABLATION PROPERTIES AND RADIATION CURABLE SENSITIZERS THEREFOR

(75) Inventors: Dean C. Webster, Fargo, ND (US); Zhigang Chen, Fargo, ND (US); Neena Ravindran, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 1043 days.

(21) Appl. No.: 11/408,801

(22) Filed: Apr. 21, 2006

(65) Prior Publication Data

US 2007/0031759 A1 Feb. 8, 2007

Related U.S. Application Data

(60) Provisional application No. 60/673,405, filed on Apr. 21, 2005.

(51) Int. Cl.
*C07D 303/00* (2006.01)
*A01N 43/20* (2006.01)
*A01N 43/24* (2006.01)

(52) U.S. Cl. ........................ 549/547; 514/475

(58) Field of Classification Search .................. 549/547; 514/475
See application file for complete search history.

(56) References Cited

U.S. PATENT DOCUMENTS

| | | | |
|---|---|---|---|
| 3,123,587 A | 3/1964 | Hogsed | |
| 3,361,546 A | 1/1968 | Raymond et al. | |
| 5,183,878 A | 2/1993 | Kanaka et al. | |
| 5,463,084 A * | 10/1995 | Crivello et al. | 549/214 |
| 5,506,014 A | 4/1996 | Minnick | |
| 5,674,922 A * | 10/1997 | Igarashi et al. | 522/168 |
| 5,840,402 A | 11/1998 | Roberts et al. | |
| 6,293,470 B1 | 9/2001 | Asplund | |
| 6,413,699 B1 | 7/2002 | Kanga | |
| 6,417,025 B1 | 7/2002 | Gengel | |
| 6,426,143 B1 | 7/2002 | Voss et al. | |
| 6,468,627 B2 | 10/2002 | Ono et al. | |

(Continued)

FOREIGN PATENT DOCUMENTS

EP 388124 9/1990

(Continued)

OTHER PUBLICATIONS

Wang et al., "Etching of Transparent Materials by Laser Ablation of an Organic Solution," *RIKEN Review*, No. 32 (Jan. 2001): Focused on Laser Precision Microfabrication (LPM2000), pp. 43-46.

(Continued)

*Primary Examiner* — Amanda C. Walke
(74) *Attorney, Agent, or Firm* — Mueting Raasch & Gebhardt, P.A.

(57) ABSTRACT

Disclosed are coating formulations that include a copolyester and a vinyl ether in which the copolyester is produced by copolymerizing a monomer composition that includes a fused aromatic diacid monomer, an unsaturated diacid monomer, and a polyol. Also disclosed are methods for producing a laser-ablatable film on a surface of a substrate. The method includes coating the substrate with a coating formulation that includes a copolyester and a vinyl ether and polymerizing the coating formulation. The copolyester includes a fused aromatic moiety covalently bonded therein. Novel radiation curable sensitizers that can be used in the preparation of radiation curable polymer films having improved laser ablation properties are also described.

21 Claims, 6 Drawing Sheets

U.S. PATENT DOCUMENTS

| | | | |
|---|---|---|---|
| 6,469,108 B2* | 10/2002 | Kuriyama et al. | 525/480 |
| 6,540,890 B1 | 4/2003 | Bhullar et al. | |
| 6,566,744 B2 | 5/2003 | Gengel | |
| 6,583,936 B1 | 6/2003 | Kaminsky et al. | |
| 6,602,790 B2 | 8/2003 | Kian et al. | |
| 6,636,363 B2 | 10/2003 | Kaminsky et al. | |
| 6,641,254 B1 | 11/2003 | Boucher et al. | |
| 6,692,646 B2 | 2/2004 | Kalt et al. | |
| 6,706,449 B2 | 3/2004 | Mikhaylik et al. | |
| 6,721,102 B2 | 4/2004 | Bourdelais et al. | |
| 6,727,970 B2 | 4/2004 | Grace et al. | |
| 6,740,900 B2 | 5/2004 | Hirai | |
| 6,762,124 B2 | 7/2004 | Kian et al. | |
| 6,774,250 B1* | 8/2004 | Hatton et al. | 549/546 |
| 6,816,380 B2 | 11/2004 | Credelle et al. | |
| 6,855,748 B1* | 2/2005 | Hatton | 522/168 |
| 6,911,235 B2 | 6/2005 | Frances et al. | |
| 7,465,531 B2* | 12/2008 | Kim et al. | 430/313 |
| 7,604,343 B2* | 10/2009 | Ishikawa | 347/102 |
| 7,615,656 B2* | 11/2009 | Kubo et al. | 549/547 |
| 7,763,182 B2* | 7/2010 | Seki et al. | 252/299.6 |
| 2002/0025991 A1* | 2/2002 | Crivello | 522/25 |
| 2003/0099825 A1 | 5/2003 | Sargeant et al. | |
| 2003/0173890 A1 | 9/2003 | Yamazaki et al. | |
| 2003/0176519 A1* | 9/2003 | Crivello | 522/7 |
| 2003/0211338 A1* | 11/2003 | Frances et al. | 428/447 |
| 2004/0004214 A1 | 1/2004 | Yamazaki et al. | |
| 2004/0007306 A1 | 1/2004 | Miyazaki et al. | |
| 2009/0184417 A1* | 7/2009 | Webster et al. | 257/729 |

FOREIGN PATENT DOCUMENTS

| | | |
|---|---|---|
| EP | 567279 | 10/1993 |
| EP | 590159 | 4/1994 |
| EP | 1434285 | 6/2004 |
| GB | 1080812 | 8/1967 |
| GB | 1305433 | 1/1973 |
| GB | 1325107 | 8/1973 |
| GB | 1441304 | 6/1976 |
| GB | 1444163 | 7/1976 |
| GB | 2390610 | 1/2004 |
| JP | 3062831 | 3/1991 |
| JP | 4130131 | 11/1992 |
| JP | 5009277 | 1/1993 |
| JP | 09241401 | 9/1997 |
| JP | 11140279 A * | 5/1999 |
| JP | 11170720 | 6/1999 |
| JP | 2001129888 | 5/2001 |
| JP | 2001200040 | 7/2001 |
| JP | 2001335384 | 12/2001 |
| JP | 2001335610 | 12/2001 |
| JP | 2002090895 | 3/2002 |
| JP | 2002105155 | 4/2002 |
| JP | 2002272042 | 9/2002 |
| JP | 2002293069 | 10/2002 |
| JP | 2002023310 | 1/2003 |
| JP | 2003040948 | 2/2003 |
| JP | 2004034606 | 2/2004 |
| JP | 2004059647 | 2/2004 |
| JP | 2004067867 | 3/2004 |
| JP | 2004182762 | 7/2004 |
| WO | 9320999 | 10/1993 |
| WO | WO 01/62835 A1 | 8/2001 |
| WO | 0189465 | 11/2001 |

OTHER PUBLICATIONS

Chen and Webster, "Cationic UV curable coatings for flexible electronic packaging (cyclaliphatic epoxide system) with laser ablation cleaness," Poster presented at the *Technology Transfer Graduate Traineeships (TTGT) Workshop 2004*. Held in Fargo, ND: Apr. 29, 2004.

Chen and Webster, "Synthesis and use of novel sensitizers to enhance laser ablation on cationic UV curable coatings," Poster presented at the *International Coatings Expo (ICE) 2004*. Held in Chicago, IL: Oct. 25-29, 2004.

Chen and Webster, "Designed carrier gas UV laser ablation sensitizers for cationic UV curable coatings," Technical Conference Proceedings—*UV & EB Technology Expo & Conference* held in Chicago, IL: Apr. 24-26, 2006. e|5 2006 Table of Contents available online [retrieved on Oct. 25, 2010]. Retrieved from the Internet: <http://www.radtech.org/publications_center/documents/RadTech2006ToC.pdf>; 8 pages.

Chen and Webster, "UV curing and UV laser ablation behavior of coatings containing novel sensitizers," Fall 2005 *PMSE preprints* 93:18-19. Papers presented at the *American Chemical Society division of Polymeric Materials: Science and Engineering Fall Meeting* held in Washington D.C.: Aug. 28-Sep. 1, 2005.

Chen and Webster, "Study of cationic UV curing and UV laser ablation behavior of coatings sensitized by novel sensitizers," May 17, 2006 *Polymer* 47(11):3715-3726. Available online on Apr. 18, 2006.

Chen and Webster, "Carrier gas UV laser ablation sensitizers for photopolymerized thin films," Jan. 25, 2007 *J. Photochem. & Photobiol. A: Chemistry* 185(2-3):115-126. Available online on Jul. 7, 2006.

Cho et al., "Dual curing of cationic UV-curable clear and pigmented coating systems photosensitized by thioxanthone and anthracene," Sep. 2003 *Polymer Testing* 22(6):633-645.

Crivello et al., "The effects of polyols as chain transfer agents and flexibilizers in photoinitiated cationic polymerization," 1986 *J. Radiation Curing* 13(4):2-6, 8-9.

Crivello and Dietliker, *Photoinitiators for free radical cationic & anionic photopolymerization*, 2$^{nd}$ Ed. John Wiley & Sons: New York, NY; 1998. Title page, publishers page, and table of contents; 6 pgs.

Crivello and Jiang, "Development of pyrene photosensitizers for cationic photopolymerizations," 2002 *Chem. Mater.* 14(11):4858-4866. Available online on Oct. 15, 2002.

Goldberg and Eaton, "Caprolactone polyols as reactive diluents for high-solids,"Nov. 1992 *Modern Paint & Coatings* 82(12):36, 39-40, and 42.

Holland and Tassinari, "Destructible electrical laminates," 1969 Technical Paper #27; *Annual Technical Conference Society Plastics and Engineering* 15:84-89.

Hua et al., "Photosensitized onium-salt-induced cationic polymerization with hydroxymethylated polynuclear aromatic hydrocarbons," 2002 *Chem. Mater.* 14(5):2369-2377. Available online on Apr. 5, 2002.

Kasapoglu and Yagci, "Photosensitized cationic polymerization of cyclohexene oxide using a phenacylanilinium salt," Jun. 2002 *Macromol. Rapid Comm.* 23(9):567-570. Available online on Jun. 28, 2002.

Koleske et al., "UV-cured cycloaliphatic epoxide coatings," presented at the 14$^{th}$ National SAMPE® Technical Conference held Oct. 12-14, 1982; *National Society for the Advancement of Material and Process Engineering (SAMPE®) Technical Conference Proceedings* 14:249-256.

Koleske et al., "Technology of cationic, UV-cured cycloaliphatic epoxides," presented at the 16$^{th}$ National SAMPE® Technical Conference held Oct. 9-11, 1984 *National Society for the Advancement of Material and Process Engineering (SAMPE®) Technical Conference Proceedings* 16:529-536.

Koleske, "Copolymerization and properties of cationic, ultraviolet light-cured cycloaliphatic epoxide systems," 1989 *Polymers Paint Colour J.* 179(4249):796-798, 800, 802, and 804.

Kunz et al., "Photoablation and microstructuring of polyestercarbonates and their blends with a XeCl excimer laser," Sep. 1998 *Appl. Phys. A: Materials Science & Processing* 67(3):347-352.

Lippert et al., "Fundamentals and applications of polymers designed for laser ablation," Jul. 2003 *Appl. Phys. A: Materials Science & Processing* 77(2):259-264. Available online on May 28, 2003.

Lippert, "Laser application of polymers," in *Advances in Polymer Science*; vol. 168—*Polymers and Light*. Lippert (Ed.): Springer-Verlag: New York, NY; 2004. Title page, publishers page, table of contencs, and pp. 51-246.

Nelson et al., "Photosensitization of cationic photopolymerizations by anthracene and its derivatives," Fall 1993 *PMSE preprints* 69:363-364. Papers presented at the *American Chemical Society Division of Polymeric Materials: Science and Engineering Fall Meeting* held in Chicago, IL.

Nuyken et al., "Excimer laser ablation of triazene-containing polyesters with different topologies," Aug. 1998 *Acta Polym.* 49(8):427-432.

Ortelli et al., "UV-Laser-Induced Decomposition of Kapton Studied by Infrared Spectroscopy," Jul. 11, 2000 *Macromolecules* 33(14):5090-5097. Available online on Jun. 13, 2000.

Ouchi et al., "Photodegradation of poly(ethylene 2,6-naphthalate) films," Jul. 1976 *J. Appl. Polym. Sci.* 20(7):1983-1987.

Sangermano et al., "Coatings obtained through cationic UV curing of epoxide systems in the presence of epoxy functionalized polybutadiene," Nov. 2002 *J. Material Sci.* 37(22):4753-4757.

Sasaki, "Oxetanes: curing properties in photo-cationic polymerization," *RadTech 2000 Proceedings*; pp. 11-15.

Wee and Park, "Laser ablation of poly(methyl methacrylate) at 266 nm," 2001 *Bull. Korean Chem. Soc.* 22(8):914-916.

\* cited by examiner

RADIATION CURABLE POLYMER FILMS HAVING IMPROVED LASER ABLATION PROPERTIES AND RADIATION CURABLE SENSITIZERS THEREFOR

The present application claims the benefit of U.S. Provisional Patent Application Ser. No. 60/673,405, filed Apr. 21, 2005, which provisional patent application is hereby incorporated by reference.

The present invention was made with the support of the Department of Defense's Defense Microelectronics Activity Grant No. DMEA90-02-C-0224. The Federal Government may have certain rights in this invention.

FIELD OF THE INVENTION

The present invention relates, generally, to polymer films having improved laser ablation properties and, more particularly, to radiation curable polymer films having improved laser ablation properties and to radiation curable sensitizers that can be useful in making such polymer films.

BACKGROUND OF THE INVENTION

UV curable polymers have developed into an important coatings research area, in part, because of their environment-friendly chemistry. While coatings based on acrylate chemistry are the dominant technology, the development of non-acrylate UV curable coatings is a growing area of research interest especially in view of the health concerns associated with acrylate chemistry. The major categories in non-acrylate technology include cationic polymerization, thiol-ene systems, and free-radical induced alternating copolymerization. These chemistries exhibit properties that are similar to acrylates with respect to cure times. Low toxicity and, perhaps more importantly, design flexibility are other benefits.

As discussed briefly above, free-radical induced alternating copolymerization is one alternative to acrylate UV curable coating. Free-radical induced alternating copolymerization takes place when an electron-rich vinyl group is mixed with an electron deficient vinyl group. This chemistry is also referred to as donor-acceptor systems. The general features of this type of polymerization are stoichiometric dependence and formation of charge-transfer complexes.

Ablative photodecomposition was discovered when high energy UV lasers were applied to polymers. One of the important applications envisaged for this process was its application as a dry-etching technique in photolithography. Higher resolution and a lower number of processing steps were the expected benefits. However, the use of standard polymers for laser ablation did not deliver the expected results. This, it is believed, is due to the lower sensitivity of polymers at the irradiation wavelength of operation.

In view of this, there is a need for methods and materials which can be used to make polymers that have improved laser ablation properties. The present invention is directed, in part, to meeting this need.

SUMMARY OF THE INVENTION

The present invention relates to a coating formulation. The coating formulation includes a copolyester and a vinyl ether. The copolyester is produced by copolymerizing a monomer composition that includes a fused aromatic diacid monomer, an unsaturated diacid monomer, and a polyol.

The present invention also relates to a method for producing a laser-ablatable film on a surface of a substrate. The method includes coating the substrate with a coating formulation that includes a copolyester and a vinyl ether and polymerizing the coating formulation. The copolyester includes a fused aromatic moiety covalently bonded therein.

The present invention also relates to a compound having the formula:

Q-L-Z where Q- represents a fused aromatic moiety; -L- represents a linking moiety; and -Z represents a moiety containing a oxetane or oxirane ring.

The present invention also relates to a compound having the formula:

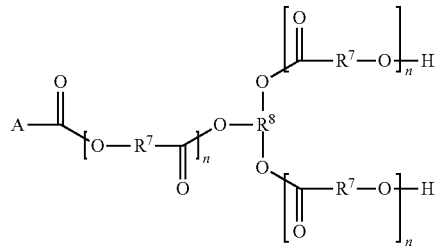

wherein A- represents a fused aromatic moiety, wherein $R^7$ represents a C2-C12 alkylene group, wherein $R^8$ represents an alkyl moiety, and wherein n is 0, 1, 2, 3, or 4.

BRIEF DESCRIPTION OF THE DRAWINGS

FIG. 1A shows a synthesis of NDC-OX by transesterification between naphthalene dicarboxylate ("NDC") and 3-ethyl-3-hydroxymethyl oxetane ("EHMO"). FIG. 1B shows a synthesis of ACA-OL by esterification of 9-anthracene carboxylic acid ("ACA") and ε-caprolactone polyol ("PCL"). FIG. 1C shows a synthesis of ACA-EP by ring-opening of 3,4-epoxycyclohex-ylmethyl-3,4-epoxycyclohexane carboxylate ("ECC") by ACA.

FIGS. 5A-5C show via depth data. FIGS. 5D-5F show via diameter data.

DETAILED DESCRIPTION OF THE INVENTION

Figure 1A:
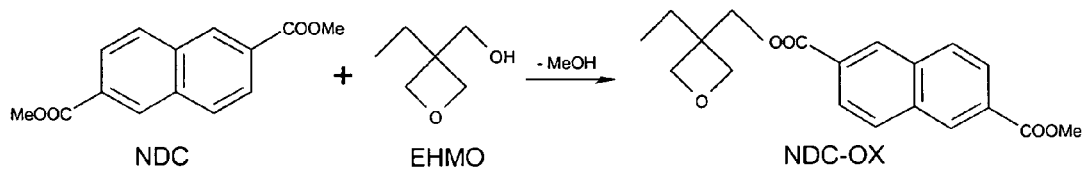
FIGS. 1A-1C are synthetic schemes that can be used to prepare various reactive sensitizers according to the present invention.

One aspect of the present invention relates to a coating formulation. The coating formulation includes a vinyl ether and a copolyester, the latter having been produced by copolymerizing a monomer composition that includes a fused aromatic diacid monomer, an unsaturated diacid monomer, and a polyol.

As used herein, "coating formulation" is meant to refer (i) to a composition which can be used to produce a coating, typically on a substrate; (ii) to a composition which has been coated onto a substrate but not yet cured; and (iii) to a composition which has been coated onto a substrate and which has been partially cured.

In the present aspect of the subject invention, the coating formulation contains a copolyester. The copolyester is the polymerization product of a fused aromatic diacid monomer, an unsaturated diacid monomer, and a polyol.

As used herein, "fused aromatic diacid monomer" is meant to refer to a monomer containing two or more acid functional groups (or groups that can be readily converted into acid functional groups, such as salts, anhydrides, etc.) that are covalently attached to a fused aromatic moiety. "Fused aromatic moiety", as used herein, is meant to refer to a ring system containing at least two unsaturated homocyclic or heterocyclic rings that are fused together so that the ring system, as a whole, is aromatic (i.e., electrons in the fused rings are delocalized). As illustrative examples of such fused aromatic moieties, there can be mentioned ring systems such as naphthalene, anthracene, phenanthrene, azulene, pyrene, quinoline, isoquinoline, acridine, and the like. Specific examples of suitable fused aromatic diacid monomers include 2,6-naphthalene dicarboxylic acid, 2,7-naphthalene dicarboxylic acid, and other naphthalene dicarboxylic acids.

As used herein, "unsaturated diacid monomer" is meant to refer to a monomer containing at least two acid functional groups (or groups that can be readily converted into acid functional groups, such as salts, anhydrides, etc.) that are covalently attached to an unsaturated moiety. Examples of unsaturated diacid monomers suitable for use in the practice of the present invention include maleic anhydride, maleic acid, fumaric acid, itaconic acid, aconitic acid, mesaconic acid, citraconic acid, dichloromaleic acid, and the like.

"Polyol", as used herein, is meant to refer to any molecule bearing two or more hydroxyl groups (or groups that can be readily converted into hydroxyl groups). Examples of polyols suitable for use in the practice of the present invention include diethylene glycol, propylene glycol, dipropylene glycol, butylene glycol, glycerol, neopentyl glycol, trimethylol propane, pentaerythritol, sorbitol, 1,6-hexanediol, 1,4-cyclohexanemethanol, 1,2-bis(hydroxyethyl)cyclohexane, and the like.

It will be appreciated that the aforementioned copolyester can be the polymerization product of a single fused aromatic diacid monomer, a single unsaturated diacid monomer, and a single polyol; or the aforementioned copolyester can be the polymerization product of a single fused aromatic diacid monomer, a single unsaturated diacid monomer, and two or more different polyols; or the aforementioned copolyester can be the polymerization product of a single fused aromatic diacid monomer, two or more different unsaturated diacid monomers, and a single polyol; or the aforementioned copolyester can be the polymerization product of two or more different fused aromatic diacid monomers, a single unsaturated diacid monomer, and a single polyol; or the aforementioned copolyester can be the polymerization product of a single fused aromatic diacid monomer, two or more different unsaturated diacid monomers, and two or more different polyols; or the aforementioned copolyester can be the polymerization product of two or more different fused aromatic diacid monomers, a single unsaturated diacid monomer, and two or more different polyols; or the aforementioned copolyester can be the polymerization product of two or more different fused aromatic diacid monomers, two or more different unsaturated diacid monomers, and a single polyol; or the aforementioned copolyester can be the polymerization product of two or more different fused aromatic diacid monomers, two or more different unsaturated diacid monomers, and two or more different polyols.

The aforementioned copolyester can be prepared by any suitable method. For example, the copolyester can be readily prepared by heating the fused aromatic diacid monomer or monomers, the unsaturated diacid monomer or monomers, and the polyol or polyols at a suitable temperature (e.g., from about 120° C. to about 300° C., such as from about 150° C. to about 270° C., from about 160° C. to about 250° C., and/or from about 180° C. to about 230° C.) for a suitable length of time (e.g., from about 1 hour to about several days, such as from about 5 hours to about 1 day and/or from about 10 hours to about 15 hours). Water produced during the OH/COOH esterification reaction can be removed using any suitable technique, such as sparging with an inert gas, like nitrogen or argon. The reaction can be carried out in the presence of a suitable catalyst, examples of which include paratoluenesulfonic acid, butylstannoic acid, dibutyl tin oxide, and stannous fluoride. The molecular weight of the polyester can range from about 100 g/mole to about 200,000 g/mole, such as from about 200 g/mole to about 100,000 g/mole, from about 500 g/mole to about 50,000 g/mole, from about 500 g/mole to about 20,000 g/mole, from about 500 g/mole to about 10,000 g/mole, from about 500 g/mole to about 5,000 g/mole, and/or from about 500 g/mole to about 2,000 g/mole.

The mole ratio of aromatic diacid monomer:unsaturated diacid monomer:polyol is typically selected such that the total number of acid groups present in the system (from the aromatic diacid monomer(s) and the unsaturated diacid monomer(s)) and the total number of hydroxyl groups present in the system (from the polyol(s)) are from about 1:5 to about 5:1, such as OH:COOH from about 1:4 to about 4:1, OH:COOH from about 1:3 to about 3:1, OH:COOH from about 1:2.5 to about 2.5:1, OH:COOH from about 1:2 to about 2:1, OH:COOH from about 1:1.5 to about 1.5:1, OH:COOH from about 1:1.4 to about 1.4:1, OH:COOH from about 1:1.3 to about 1.3:1, OH:COOH from about 1:1.2 to about 1.2:1). Illustratively, where the aromatic diacid monomer(s) each contain two carboxylic acid functional groups, where the unsaturated diacid monomer(s) each contain two carboxylic acid functional groups, and where the polyol(s) each contain 3 hydroxyl groups, the number of moles of polyol can be selected such that it is from about 7 to about 0.2 times (such as from about 6 to about 0.3 times, from about 4 to about 0.4 times, from about 3 to about 0.5 times, from about 2.7 to about 0.6 times, from about 2 to about 0.8 times, from about 1.9 to about 0.9 times, from about 1.8 to about 1 times, and/or from about 1.6 to about 1.1 times) the sum of the number of moles of unsaturated diacid monomer(s) and the number of moles of aromatic diacid monomer(s). The hydroxyl:acid ratio can be intentionally varied to control the molecular weight of the polymer. Generally, the larger the ratio (either way), the lower the molecular weight of the polymer. If the ratio of OH:COOH or COOH:OH is very close to 1:1 (for example, as in the case where OH:COOH is from 1.08:1 to 1:1.08, such as from 1.05:1 to 1:1.05 from 1.02:1 to 1:02.1, and/or from 1.01:1 to 1:1.01), a high molecular weight polymer may be obtained. Such high molecular weight polymers can be difficult to use in coating formulations due to their high viscosity. Molecular weight (and, thus, viscosity) can be controlled by using a non-stoichiometric ratio of OH:COOH, for example, as in the case where OH:COOH is from about 1:1.1 to about 1:5 (such as from about 1:1.1 to about 1:4, from about 1:1.1 to about 1:3, from about 1:1.1 to about 1:2.25, from about 1:1.1 to about 1:2, from about 1:1.1 to about 1:1.5, from about 1:1.1 to about 1:1.4, from about 1:1.1 to about 1:1.3, from about 1:1.15 to about 1:1.25, and/or about 1:1.2) or as in the case where COOH:OH is from about 1:1.1 to about 1:5 (such as from about 1:1.1 to about 1:4, from about 1:1.1 to about 1:3, from about 1:1.1 to about 1:2.25, from about 1:1.1 to about 1:2, from about 1:1.1 to about 1:1.5, from about 1:1.1 to about 1:1.4, from about 1:1.1 to about 1:1.3, from about 1:1.15 to about 1:1.25, and/or about 1:1.2). Suitable mole ratios of aromatic diacid monomer:unsaturated diacid monomer are from about 20:1 to about 1:20, such as from about 15:1 to about 1:15, from about 10:1 to about 1:10, from about 5:1 to about 1:5, from about 4:1 to about 1:4, from about 3:1 to about 1:3, and/or from about 2:1 to about 1:2.

As discussed above, the coating formulation of the present invention, in addition to containing a copolyester (as discussed above), also contains a vinyl ether. "Vinyl ether", as used herein, is meant to include monovinyl ethers, divinyl ethers, trivinyl ethers, tetravinyl ethers, and so forth. Illustrative monovinyl ethers that can be used in the practice of the present invention include ethyl vinyl ether, methyl vinyl ether, propyl vinyl ether, and the like. Examples of suitable divinyl ethers include divinyl ether, ethylene glycol divinyl ether, 1,6-hexanediol divinyl ether, and the like. Suitable trivinyl ethers include glycerol trivinyl ether, trimethylolpropane trivinyl ether, and the like. One example of a suitable tetravinyl ethers is pentaerythritol tetravinyl ether. Combination of these and other vinyl ethers can also be employed, and the phrase "a vinyl ether", as used herein, is meant to include such combinations.

The aforementioned coating formulation can contain other materials in addition to the aforementioned copolyester(s) and vinyl ether(s). For example, the coating formulation can include a suitable photoinitiator, such as Darocur 1173 (2-hydroxy-2-methyl-1-phenyl-propan-1-one).

The coating formulation can be cast into a film by a variety of techniques, including spraying, brushing, spin casting, or through the use of a Doctor blade or similar applicator. The thickness of the film can be from about 1 micron to about 250 microns, such as from about 1 micron to about 5 microns, from about 2 microns to about 4 microns, from about 1 micron to about 10 microns, from about 2 microns to about 10 microns, about 2 microns, from about 3 microns to about 4 microns, about 3.5 microns, from about 2 microns to about 200 microns, from about 10 microns to about 150 microns, from about 50 microns to about 125 microns, and/or about 100 microns.

The aforementioned coating formulation, for example, cast into a film form, can be cured or otherwise polymerized, for example, by exposure to UV radiation, and the present invention, in another aspect thereof, relates to polymers produced by such a curing or other polymerization process.

In yet another aspect thereof, the present invention relates to an electronic device. The electronic device includes an electronic chip that has at least one substantially planar surface. A polymeric coating is disposed on the electronic chip's substantially planar surface. The polymeric coating includes a polymer prepared by polymerizing a coating formulation according to the present invention. The electronic device may include other electronic components, such as resistors, capacitors, transistors, diodes, integrated circuits or other electronic chips, and power supplies. Where the electronic device includes other electronic components, these other electronic components can either be coated with a polymeric coating as described above or not.

The electronic device can further include a hole disposed through the polymeric coating and a signal transmitting element (e.g., a wire, solder ball, or other electrically conductive element; an optical waveguide or other an optically conductive element; etc.) disposed through the hole and connected (e.g., by solder, by an suitable adhesive, such as a conducting epoxy adhesive, etc.) to the electronic chip. It will be appreciated that "a hole", as used herein, is meant to refer to one or more holes, and that "a signal transmitting element", as used herein, is meant to refer to one or more signal transmitting elements (which can be of the same type or different types). The aforementioned hole (or holes) can be conveniently formed by laser ablation, for example by using a laser having a UV output, such as a UV output of from about 300 nm to about 400 nm, from about 310 nm to about 390 nm, from about 320 nm to about 380 nm, from about 330 nm to about 370 nm, and/or from about 340 nm to about 360 nm. Illustratively, a solid tripled pulsed YAG laser having an output of 355 nm can be employed. The number of pulses can be adjusted to ablate the polymeric coating to the desired depth. For example, where the polymeric coating is disposed on the surface of an electronic chip, the depth of ablation is usually equal to the thickness of the coating.

In yet another aspect thereof, the present invention relates to a method for producing a laser-ablatable film on a surface of a substrate. The method includes coating the substrate with a coating formulation of the present invention and curing or otherwise polymerizing the coating formulation. Suitable substrates include one or more surfaces of electronic chips; suitable methods for coating the substrate with the coating formulation include those described above in regard to coating electronic chips; and suitable methods for curing or otherwise polymerizing the coating formulation include those described above in regard to coating electronic chips.

In yet another aspect thereof, the present invention relates to a method for producing a pre-selected pattern on a surface of a substrate. The method includes producing a laser-ablatable film on a surface of a substrate in accordance with a method according to the present invention and exposing the film to ultraviolet electromagnetic radiation under conditions effective to ablate a portion of the film to produce the preselected pattern. The preselected pattern can be a hole or a plurality of holes arranged in a particular fashion, for example, so as to permit wires, solder balls, or other signal transmitting elements to be connected with the substrate at particular locations. Alternatively, the preselected pattern can be a pattern of ridges and valleys, where the valleys can (but need not) be of a depth which exposes the substrate. Still alternatively, the preselected pattern can be a relief similar to relief wood carving but where the medium is not wood but, instead, the laser-ablatable film.

In yet another aspect thereof, the present invention relates to a method for producing a laser-ablatable film on a surface of a substrate. The method includes coating the substrate with a coating formulation comprising a copolyester and a vinyl ether and curing or otherwise polymerizing the coating formulation. The copolyester used in this method includes a fused aromatic moiety covalently bonded therein. Examples of suitable copolyesters and vinyl ethers that can be used in this aspect of the present invention include those discussed hereinabove. Examples of suitable methods for coating the substrate with a coating formulation include spraying, brushing, spin casting, as well as methods which employ a Doctor blade or similar applicator. The thickness of the film can be from about 1 micron to about 250 microns, such as from about 1 micron to about 5 microns, from about 2 microns to about 4 microns, from about 1 micron to about 10 microns, from about 2 microns to about 10 microns, about 2 microns, from about 3 microns to about 4 microns, about 3.5 microns, from about 2 microns to about 200 microns, from about 10 microns to about 150 microns, from about 50 microns to about 125 microns, and/or about 100 microns. Examples of suitable methods for curing or otherwise polymerizing the coating formulation include exposing the coating formulation to electromagnetic radiation, such as ultraviolet radiation. In this regard, it should be noted that the coating formulation can contain other materials, such as photoinitiators.

The laser-ablatable film thus produced on the surface of a substrate can be used in a method for producing a pre-selected pattern on a surface of a substrate, to which method the present invention also relates. The method involves producing a laser-ablatable film on a surface of a substrate (in accordance with a method of the present invention) and exposing the film to ultraviolet electromagnetic radiation under conditions effective to ablate a portion of the film to produce the pre-selected pattern. In this regard, "conditions effective to ablate a portion of the film to produce the pre-selected pattern" are meant to refer to altering the intensity, duration, numbers of pulses, etc., of the ultraviolet electromagnetic radiation so as to ablate various portions of the laser-ablatable film to various depths. This can be done, for example, by scanning the ultraviolet electromagnetic laser beam (or other radiation) over the surface of the film in a raster-like motion and changing the intensity, duration, numbers of pulses, etc. as the ultraviolet electromagnetic laser beam exposes a particular portion of the substrate. Additionally or alternatively, this can be done by the use of masks or other techniques well known in the art of photolithography.

As will be evident from the above discussion, the aforementioned coating formulations, polymers, and methods of the present invention can be advantageously employed in the production of electronic chips by providing a method for readily forming holes, vias, or other openings in a photopolymerized packaging layer for receiving conductive elements, such as solder balls. Examples of methods for making electronic chips in which the aforementioned coating formulations, polymers, and methods of the present invention can be employed include those which involve fluidic self assembly (e.g., as described in U.S. Pat. No. 6,417,025 to Gengel; U.S. Pat. No. 6,417,025 to Gengel; U.S. Pat. No. 6,566,744 to Gengel, which are hereby incorporated by reference). Still other examples of methods for making electronic chips in which the aforementioned coating formulations, polymers, and methods of the present invention can be employed include those which are described in U.S. Pat. No. 6,816,380 to Credelle et al., which is hereby incorporated by reference.

The present invention, in yet another aspect thereof, relates to a compound having the formula:

Q-L-Z

In the above formula, Q- represents a fused aromatic moiety. As discussed above, "fused aromatic moiety", as used herein, is meant to refer to a ring system containing at least two unsaturated homocyclic or heterocyclic rings that are fused together so that the ring system, as a whole, is aromatic (i.e., electrons in the fused rings are delocalized). As illustrative examples of such fused aromatic moieties, there can be mentioned naphthalene moieties, anthracene moieties, and pyrene moieties. As other illustrative examples of such fused aromatic moieties, there can be mentioned ring systems such as phenanthrene, azulene, quinoline, isoquinoline, acridine, and the like.

In the above formula, -Z represents a moiety containing a oxetane or oxirane ring. Illustratively, Z can be a moiety having the formula:

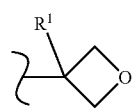

where $R^1$ represents a hydrogen atom or a substituted or unsubstituted alkyl group, such as a substituted lower alkyl group, an unsubstituted lower alkyl group, a substituted C1-C6 alkyl group, an unsubstituted C1-C6 alkyl group, a substituted C1-C4 alkyl group, an unsubstituted C1-C4 alkyl group, a methyl group, an ethyl group, a propyl group, etc. Alternatively, -Z can be a moiety which contains an oxirane ring fused to a cycloalkyl ring, such as C5 or C6 cycloalkyl ring, for example, as in the case where -Z has the formula:

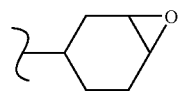

In the above formula, -L- represents a linking moiety, such as an alkylene group, an arylene group, and linking groups based on one or more carboxylate ester moieties. As one example of linking groups based on one or more carboxylate ester moieties, there can be mentioned groups having the formula:

—C(O)—O—R²— where $R^2$ is an alkylene group. Illustrative examples of suitable $R^2$ alkylene groups include substituted lower alkylene groups, unsubstituted lower alkylene groups, substituted C1-C6 alkylene groups, unsubstituted C1-C6 alkylene groups, substituted C1-C4 alkylene groups, unsubstituted C1-C4 alkylene groups, methylene groups, ethylene group, propylene group, etc. As another example of linking groups based on one or more carboxylate ester moieties, there can also be mentioned groups having the formula:

—C(O)—O—R⁴—C(O)—O—R³— where $R^3$ and $R^4$ independently represent the same or different alkylene groups. Illustrative examples of suitable $R^3$ and $R^4$ alkylene groups include those which are linear as well as those which are cyclic. Examples of suitable $R^3$ and $R^4$ linear alkylene groups include substituted linear lower alkylene groups, unsubstituted linear lower alkylene groups, substituted linear C1-C6 alkylene groups, unsubstituted linear C1-C6 alkylene groups, substituted linear C1-C4 alkylene groups, unsubstituted linear C1-C4 alkylene groups, methylene groups, ethylene group, propylene group, etc. Examples of suitable $R^3$ and $R^4$ cyclic alkylene groups include substituted cyclic lower alkylene groups, unsubstituted cyclic lower alkylene groups, substituted cyclic C4-C12 alkylene groups, unsubstituted cyclic C4-C12 alkylene groups, substituted cyclic C5-C8 alkylene groups, unsubstituted cyclic C5-C8 alkylene groups, substituted cyclic C5-C6 alkylene groups, unsubstituted cyclic C5-C6 alkylene groups, substituted cyclic C6 alkylene groups, unsubstituted cyclic C6 alkylene groups, substituted cyclohex-1,4-diyl groups, and unsubstituted cyclohex-1,4-diyl groups. Illustratively, the linking group, -L-, can have the formula:

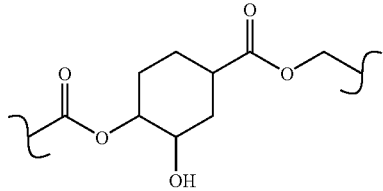

In one embodiment of this aspect of the present invention, Q- represents a substituted fused aromatic moiety having the formula:

wherein -Q'- represents a fused aromatic moiety; -L'- represents a linking moiety; and Z'- represents a moiety containing a oxetane or oxirane ring. It should be noted that -L'- can be the same as -L-, or it can be different. Likewise, it should be noted that Z'- can be the same as -Z (as in the case where Z'- and -Z represent the same oxetane or oxirane ring), or it can be different (as in the case where Z'- represents an oxetane ring and where -Z represents an oxirane ring; or where Z'- represents an oxirane ring and where -Z represents an oxetane ring; or as in the case where Z'- represents a first oxirane ring and where -Z represents an second, different oxirane ring; or as in the case where Z'- represents a first oxetane ring and where -Z represents an second, different oxetane ring). Illustratively, the compound of this aspect of the present invention can have the formula:

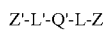

where -Q'- represents a fused aromatic moiety; -L'- represents a linking moiety; and Z'- represents a moiety containing a oxetane or oxirane ring, as discussed further hereinabove and hereinbelow.

Illustrative examples of compounds of the present invention having the formula Q-L-Z include those having the formula:

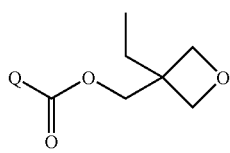

where Q- represents a fused aromatic moiety, for example, as discussed above. In some embodiments, such compounds have the formula:

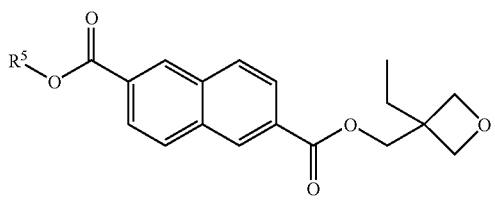

where $R^5$ represents a substituted or unsubstituted alkyl group, such as a substituted lower alkyl group, an unsubstituted lower alkyl group, a substituted C1-C6 alkyl group, an unsubstituted C1-C6 alkyl group, a substituted C1-C4 alkyl group, an unsubstituted C1-C4 alkyl group, a methyl group, an ethyl group, a propyl group, etc. In other embodiments, such compounds have the formula:

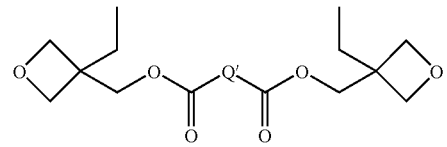

where -Q'- represents a fused aromatic moiety, such as a naphthalene moiety (e.g., a 2,6-naphthalene moiety, a 2,7-naphthalene moiety), an anthracene moiety, a pyrene moiety, etc. Illustratively, one such compound has the formula:

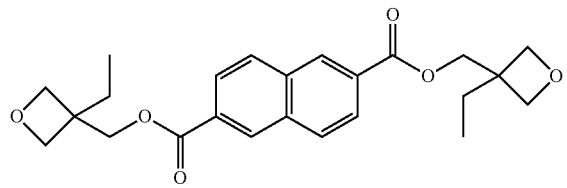

Other illustrative examples of compounds of the present invention having the formula Q-L-Z include those having the formula:

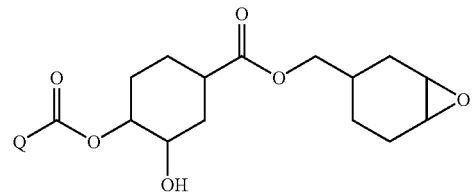

where Q- represents a fused aromatic moiety, for example, as discussed above. Illustratively, one such compound has the formula:

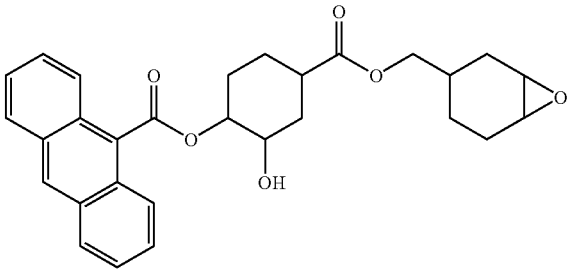

The aforementioned compounds of the present invention having the formula Q-L-Z can be prepared by any suitable method.

For example, the aforementioned compounds can be synthesized by transesterification, illustratively, by contacting an ester having the formula Q-COOR$^6$ with an alcohol having the formula HO-Z under conditions effective to effect transesterification. In the ester having the formula Q-COOR$^6$, $R^6$ can be a substituted or unsubstituted alkyl group, such as a substituted or unsubstituted linear or cyclic alkyl group, a substituted linear lower alkyl group, an unsubstituted linear lower alkyl group, a substituted linear C1-C6 alkyl group, an unsubstituted linear C1-C6 alkyl group, a substituted linear C1-C4 alkyl group, an unsubstituted linear C1-C4 alkyl group, a methyl group, an ethyl group, a propyl group, etc., a substituted cyclic lower alkyl group, an unsubstituted cyclic lower alkyl group, a substituted cyclic C5-C8 alkyl group, an unsubstituted cyclic C5-C8 alkyl group, a substituted cyclic C5-C6 alkyl group, an unsubstituted cyclic C5-C6 alkyl, a substituted cyclic C6 alkyl group, an unsubstituted cyclic C6 alkyl group, a cyclohexyl group, etc. The transesterification reaction can be advantageously carried out by heating the mixture of ester having the formula Q-COOR$^6$ and alcohol having the formula HO-Z, illustratively at from about 50° C. to about 150° C., such as at about 100° C., for from about 2 hours to about 5 days, such as for from about 12 hours to about 2 days and/or for about 1 day. The transesterification reaction can be carried out in a suitable solvent, such as an aromatic solvent (e.g., benzene, toluene, and/or xylene). Advantageously, the R$^6$—OH transesterification byproduct can be removed, for example, to drive the transesterification reaction to completion. Removal of the R$^6$—OH by product can be carried out, for example, by using a low molecular weight R$^6$ moiety, such that the R$^6$—OH byproduct has a boiling point below the temperature at which the reaction is carried out. The transesterification reaction can also be advantageously carried out in the presence of a suitable transesterification catalyst, such as a tertiary amine. Examples of suitable tertiary amine transesterification catalysts include tertiary amine-containing ion exchange resins, such as an ion exchange resin having alkyl tertiary amine functionality, one example of which is AMBERLYST™ A-21 ion exchange resin (available from Aldrich, Milwaukee, Wis.). The reaction mixture can be stirred or otherwise agitated, and the transesterification reaction is advantageously carried out with an inert gas (e.g., nitrogen, argon, etc.) purge. The ratio of starting materials is not particularly critical to the synthesis. Suitable mole ratios of ester having the formula Q-COOR$^6$ to alcohol having the formula HO-Z include mole ratios ranging from about 1:5 to about 5:1, such as from about 4:1 to about 1:4, from about 3:1 to about 1:3, from about 2:1 to about 1:2, about 1:1.5, about 1:2, about 1:2.5, about 1:3, from about 1:1 to about 1:2, from about 1:1 to about 1:2.5, from about 1:1 to about 1:3, from about 1:1 to about 1:4, from about 1:1 to about 1:5 from about 1:1.5 to about 1:2, from about 1:1.5 to about 1:2.5, from about 1:1.5 to about 1:3, from about 1:1.5 to about 1:4, and/or from about 1:1.5 to about 1:5.

Still alternatively, the aforementioned compounds of the present invention having the formula Q-L-Z can be synthesized by an epoxide ring opening reaction. Illustratively, compounds of the present invention having the formula:

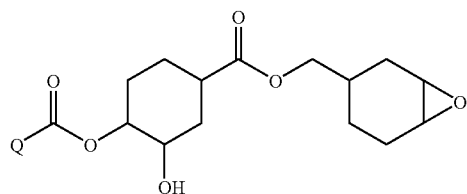

(where Q- represents a fused aromatic moiety, for example, as discussed above), such as a compound having the formula:

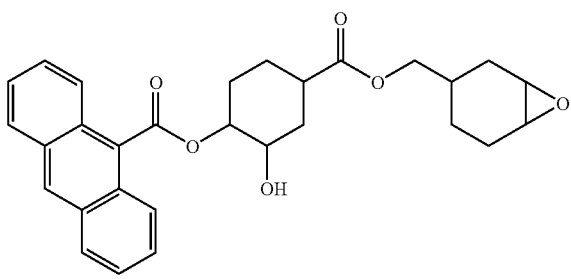

can be prepared by reacting an acid having the formula Q-COOH with a difunctional cycloaliphatic epoxide, for example, a 3,4-epoxycyclohexylmethyl-3,4-epoxycyclohexane carboxylate, such as a difunctional cycloaliphatic epoxide having the following formula

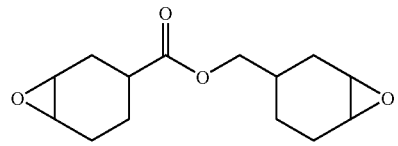

which is available from Dow Chemical Company as CRYACURE™ UVR 6110. The reaction can be advantageously carried out by heating the mixture of acid having the formula Q-COOH and difunctional cycloaliphatic epoxide (e.g., a 3,4-epoxycyclohexylmethyl-3,4-epoxycyclohexane carboxylate), illustratively at from about 50° C. to about 180° C., such as at from about 100° C. to about 140° C. and/or at about 120° C., for from about 1 hour to about 3 days, such as for from about 4 hours to about 2 days, for from about 12 hours to about 1 day, and/or for about 18 hours. The reaction can be carried out in a suitable solvent, such as an aromatic solvent (e.g., benzene, toluene, and/or xylene). The reaction can be advantageously carried out with stirring or other forms of agitation. The ratio of starting materials is not particularly critical to the synthesis. Suitable mole ratios of acid having the formula Q-COOH to difunctional cycloaliphatic epoxide (e.g., a 3,4-epoxycyclohexylmethyl-3,4-epoxycyclohexane carboxylate) include mole ratios ranging from about 1:5 to about 5:1, such as from about 4:1 to about 1:4, from about 3:1 to about 1:3, from about 2:1 to about 1:2, from about 1.5:1 to about 1:1.5, from about 1.3:1 to about 1:1.3, from about 1.2:1 to about 1:1.2, from about 1.1:1 to about 1:1.1, and/or about 1:1.

The present invention also relates to compositions which include the aforementioned compounds of the present invention having the formula Q-L-Z (as described above) and a polyol.

As discussed above, "polyol" is meant to refer to any molecule bearing two or more hydroxyl groups (or groups that can be readily converted into hydroxyl groups) as well as to combinations of such molecules. Examples of polyols suitable for use in the compositions of the present invention include diethylene glycol, propylene glycol, dipropylene glycol, butylene glycol, glycerol, neopentyl glycol, trimethylol propane, pentaerythritol, sorbitol, 1,6-hexanediol, 1,4-cyclohexanemethanol, 1,2-bis(hydroxyethyl)cyclohexane, and the like. Combinations of these and other polyols can also be used.

In addition to containing a compound of the present invention having the formula Q-L-Z and a polyol, these compositions of the present invention can further include other materials. Illustratively and especially where the composition is to be used as a coating formulation, these compositions can further include difunctional oxetane/oxirane resins, other monofunctional oxetane/oxirane resins, other compounds bearing a single hydroxyl function, photoinitiators, and the like.

As an example of a suitable difunctional oxetane/oxirane resin that can be used in such compositions of the present invention, there can be mentioned 3,4-epoxycyclohexylmethyl-3,4-epoxycyclohexane carboxylates, such as a difunctional cycloaliphatic epoxide having the following formula:

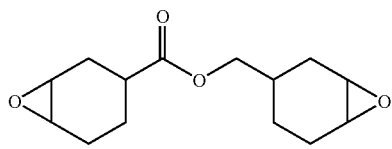

which is available from Dow Chemical Company as CRYACURE™ UVR 6110. Other suitable difunctional oxetane/oxirane resin that can be used in such compositions include various commercially available difunctional oxetane reactive diluents, such as bis([1-ethyl(3-oxetanyl)]methyl)ether, which is available from Toagosei Co. Ltd. (Tokyo, Japan) as OXT-221.

Examples of monofunctional oxetane/oxirane resins that can be used in such compositions of the present invention include various commercially available monofunctional oxetane reactive diluents (such as 3-ethyl-3-hydroxymethyl oxetane, which is available from Dow Chemical Company as CRYACURE™ UVR 6000) and various commercially available monofunctional oxirane reactive diluents (such as a methyl or other ester of 3,4-epoxycyclohexane carboxylic acid, the methyl ester of which is available from Dow Chemical Company as ERL-4140).

As one skilled in the art will appreciate, the selection and amounts of difunctional oxetane/oxirane resins, other monofunctional oxetane/oxirane resins, and/or compounds bearing a single hydroxyl function, relative to the amount of compound of the present invention having the formula Q-L-Z and relative to the amount of polyol can depend on the desired characteristics of the composition and the desired characteristics of the polymer to be produced by polymerization of the composition. For example, where the composition is to be used as a coating formulation, the various components and their respective amounts can be chosen based on the desired characteristics of the coating formulation (e.g., rheology, stability, etc.) and the desired characteristics of the coating to be produced by polymerization of the coating formulation (e.g., hardness, stability, etc.). The mole ratio of compound Q-L-Z:polyol:difunctional oxetane/oxirane resins:other monofunctional oxetane/oxirane resins:compounds bearing a single hydroxyl function is typically selected such that the total number of hydroxyl groups present in the system (e.g., from the polyol and from the compounds bearing a single hydroxyl function) and the total number of oxetane/oxirane groups present in the system (e.g., from the compound Q-L-Z, from other monofunctional oxetane/oxirane resins, and from difunctional oxetane/oxirane resins) are substantially the same (e.g., oxetane/oxirane:hydroxyl from about 1:1.2 to about 1.2:1, such as oxetane/oxirane:hydroxyl from about 1:1.1 to about 1.1:1, oxetane/oxirane:hydroxyl from about 1:1.05 to about 1.05:1, and/or oxetane/oxirane:hydroxyl about 1:1). Suitable mole ratios of compound Q-L-Z:polyols are from about 10000:1 to about 1:10000, such as from about 5000:1 to about 1:5000, from about 2000:1 to about 1:2000, from about 1000:1 to about 1:1000, from about 500:1 to about 1:500, from about 200:1 to about 1:200, from about 100:1 to about 1:100, from about 50:1 to about 1:50, from about 20:1 to about 1:20, from about 10:1 to about 1:10, and/or from about 5:1 to about 1:5.

As discussed above, the compositions can further include a photoinitiator, such as a cationic photoinitiator. Examples of suitable photoinitiators include antimony-containing cationic photoinitiator, such as a triarylsulfonium hexafluoroantimonate salt (e.g., mixed triarylsulfonium hexafluoroantimonate salt in propylene carbonate, available from Dow Chemical Company).

The present invention, in yet another aspect thereof, relates to a compound having the formula ("Formula I"):

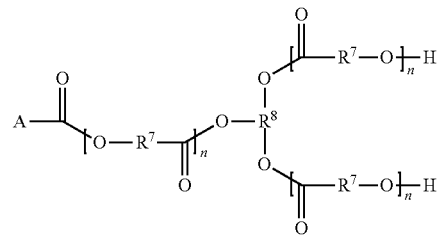

In Formula I, n is 0, 1, 2, 3, or 4, and A- represents a fused aromatic moiety. As discussed above, "fused aromatic moiety", as used herein, is meant to refer to a ring system containing at least two unsaturated homocyclic or heterocyclic rings that are fused together so that the ring system, as a whole, is aromatic (i.e., electrons in the fused rings are delocalized). As illustrative examples of such fused aromatic moieties, there can be mentioned naphthalene moieties, anthracene moieties, and pyrene moieties. As other illustrative examples of such fused aromatic moieties, there can be mentioned ring systems such as phenanthrene, azulene, quinoline, isoquinoline, acridine, and the like. Illustratively the compound can have the formula

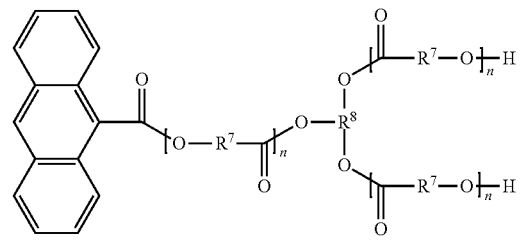

In Formula I, $R^7$ represents a C2-C12 alkylene group, which alkylene group can be substituted or unsubstituted. Where $R^7$ represents a substituted C2-C12 alkylene group, suitable substituents include alkyl groups, aryl groups, hydroxy groups, alkoxy groups, and/or halogen atoms. Illustratively, $R^7$ can be a substituted or unsubstituted C2-C8 alkylene group; a substituted or unsubstituted C3-C6 alkylene group; a substituted or unsubstituted C2, C3, C4, C5, C6, C7, C8, C9, C10, C11, or C12 alkylene group; an alkylene group having the formula —$(CH_2)_m$—, where m is 1, 2, 3, 4, 5, 6, 7, 8, 9, 10, 11, or 12; ad/or an alkylene group having the formula —$(CH_2)_5$—.

In Formula I, $R^8$ represents an alkyl moiety, such as an alkyl moiety having the formula $R^{10}$—C(—$R^9$—)$_3$, where $R^{10}$ represents a substituted or unsubstituted alkyl group and $R^9$ is a C1-C12 substituted or unsubstituted alkylene group. Where $R^9$ and/or $R^{10}$ are substituted, suitable substituents include alkyl groups, aryl groups, hydroxy groups, alkoxy groups, and/or halogen atoms. In certain embodiments, $R^{10}$ can be an alkyl group having the formula $H_3C$—$R^9$—, for example, as in the case where $R^{10}$ is an alkyl group having the formula $H_3C$—$R^9$— and $R^9$ is a substituted or unsubstituted C1-C6 alkylene group, a substituted or unsubstituted C1-C3 alkylene group. As further illustration, $R^8$ can be an alkyl moiety having the formula $R^{10}$—C(—$R^9$—)$_3$, wherein $R^{10}$— is a substituted or unsubstituted C1-C6 alkyl group (e.g., a substituted or unsubstituted C1, C2, C3, C4, C5, or C6 alkyl group) and wherein —$R^9$— is a substituted or unsubstituted C1-C3 alkylene group (e.g., a substituted or unsubstituted C1, C2, or C3) alkylene group, such as in the case where $R^{10}$— is a substituted or unsubstituted C2 alkyl group and where $R^9$ is a substituted or unsubstituted C1 alkylene group or as in the case where $R^{10}$— is a substituted or unsubstituted C1-C4 alkyl group and where $R^9$ is an alkylene group having the formula —$CH_2$—.

Illustratively, the compounds of Formula I can have the following formula:

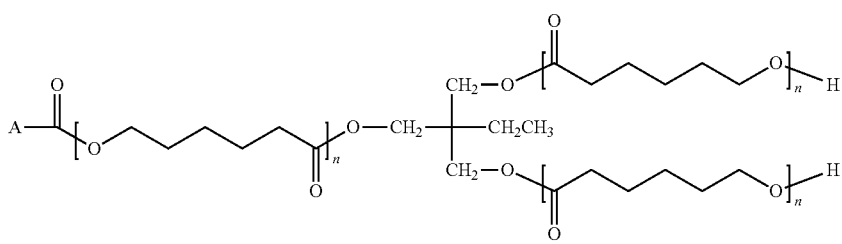

where A- represents a fused aromatic moiety and where n is 0, 1, 2, 3, or 4. As still further illustration, the compounds of Formula I can have the following formula:

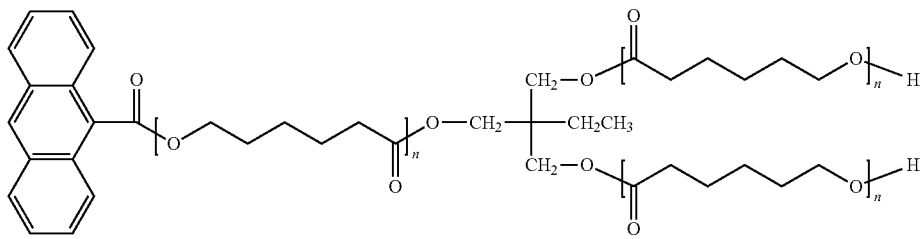

where n is 0, 1, 2, 3, or 4.

The aforementioned compounds of the present invention having Formula I can be prepared by any suitable method. For example, the aforementioned compounds can be synthesized by contacting an acid having the formula A-COOH with a polyol, such as a polyol having the formula:

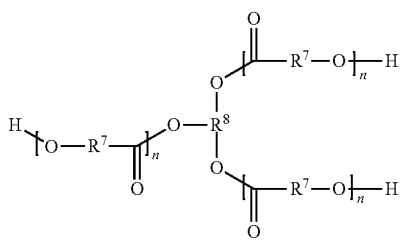

under conditions effective to effect esterification. The reaction can be advantageously carried out by heating the mixture of ester having the formula A-COOH and polyol, illustratively at from about 50° C. to about 180° C., such as at from about 100° C. to about 140° C. and/or at about 120° C., for from about 1 hour to about 4 days, such as for from about 4 hours to about 3 days, for from about 12 hours to about 36 hours, for from about 1 day to about 3 days, for from about 18 hours to about 36 hours, for from about 2 days to about 36 hours, and/or for about 29 hours. The reaction can be carried out in a suitable solvent, such as an aromatic solvent (e.g., benzene, toluene, and/or xylene). Advantageously, the water byproduct can be removed, for example, to drive the esterification reaction to completion. Removal of the water byproduct can be carried out, for example, by using a suitable drying agent or by purging with an inert gas (e.g., nitrogen, argon, etc.). The esterification reaction can also be advantageously carried out in the presence of a suitable esterification catalyst, such as a compound having sulfonic acid functionality. Examples of suitable sulfonic acid esterification catalysts include sulfonic acid-containing ion exchange resins, such as AMBERLYST™ A-15 ion exchange resin (available from Aldrich, Milwaukee, Wis.). The reaction mixture can be stirred or otherwise agitated. The ratio of starting materials is not particularly critical to the synthesis. Suitable mole ratios of acid having the formula A-COOH to polyol include mole ratios ranging from about 1:5 to about 5:1, such as from about 4:1 to about 1:4, from about 3:1 to about 1:3, from about 2:1 to about 1:2, from about 1.5:1 to about 1:1.5, from about 1.3:1 to about 1:1.3, from about 1.2:1 to about 1:1.2, from about 1.1:1 to about 1:1.1, and/or about 1:1.

The present invention also relates to compositions which include the aforementioned compounds of the present invention (i.e., those of Formula I, as described above) and a difunctional oxetane/oxirane resin.

"Difunctional oxetane/oxirane resin", as used herein, is meant to refer to any molecule bearing two or more oxetane and/or oxirane groups, as well as to combinations of such molecules. Illustratively, "difunctional oxetane/oxirane resin", as used herein, is meant to include molecules that bear at least two oxirane groups, molecules that bear at least two oxetane groups, as well as molecules that bear at least one oxetane group and at least one oxirane group. Examples of suitable difunctional oxirane resins that can be used in the composition of the present invention, include 3,4-epoxycyclohexylmethyl-3,4-epoxycyclohexane carboxylates (such as a difunctional cycloaliphatic epoxide having the following formula:

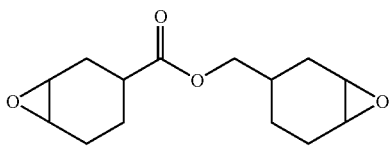

which is available from Dow Chemical Company as CRYA-CURE™ UVR 6110) and various commercially available difunctional oxetane reactive diluents, such as bis([1-ethyl(3 oxetanyl)]methyl)ether (which is available from Toagosei Co. Ltd., Tokyo, Japan, as OXT-221).

In addition to containing a compound of the present invention of Formula I and a difunctional oxetane/oxirane resin, these compositions of the present invention can further include other materials. Illustratively and especially where the composition is to be used as a coating formulation, these compositions can further include monofunctional oxetane/oxirane resins, other polyols, compounds bearing a single hydroxyl function, photoinitiators, and the like.

As examples of other polyols that can be included in these compositions of the present invention, there can be mentioned diethylene glycol, propylene glycol, dipropylene glycol, butylene glycol, glycerol, neopentyl glycol, trimethylol propane, pentaerythritol, sorbitol, 1,6-hexanediol, 1,4-cyclohexanemethanol, 1,2-bis(hydroxyethyl)cyclohexane, and the like. Combinations of these and other polyols can also be used.

Examples of monofunctional oxetane/oxirane resins that can be used in such compositions include various commercially available monofunctional oxetane reactive diluents (such as 3-ethyl-3-hydroxymethyl oxetane, which is available from Dow Chemical Company as CRYACURE™ UVR 6000) and various commercially available monofunctional oxirane reactive diluents (such as a methyl or other ester of 3,4-epoxycyclohexane carboxylic acid, the methyl ester of which is available from Dow Chemical Company as ERL-4140).

As one skilled in the art will appreciate, the selection and amounts of other polyols, monofunctional oxetane/oxirane resins, and/or compounds bearing a single hydroxyl function, relative to the amount of compound of the present invention of Formula I and relative to the amount of difunctional oxetane/oxirane resin can depend on the desired characteristics of the composition and the desired characteristics of the polymer to be produced by polymerization of the composition. For example, where the composition is to be used as a coating formulation, the various components and their respective amounts can be chosen based on the desired characteristics of the coating formulation (e.g., rheology, stability, etc.) and the desired characteristics of the coating to be produced by polymerization of the coating formulation (e.g., hardness, stability, etc.). The mole ratio of compound of Formula I:difunctional oxetane/oxirane resin:other polyols:monofunctional oxetane/oxirane resins:compounds bearing a single hydroxyl function is typically selected such that the total number of hydroxyl groups present in the system (e.g., from the compound of Formula I, from the other polyols, and from the compounds bearing a single hydroxyl function) and the total number of oxetane/oxirane groups present in the system (e.g., from the difunctional oxetane/oxirane resins and from the monofunctional oxetane/oxirane resins) are substantially the same (e.g., oxetane/oxirane:hydroxyl from about 1:1.2 to about 1.2:1, such as oxetane/oxirane:hydroxyl from about 1:1.1 to about 1.1:1, oxetane/oxirane:hydroxyl from about 1:1.05 to about 1.05:1, and/or oxetane/oxirane:hydroxyl about 1:1). Suitable mole ratios of compound Formula I:difunctional oxetane/oxirane resins are from about 10000:1 to about 1:10000, such as from about 5000:1 to about 1:5000, from about 2000:1 to about 1:2000, from about 1000:1 to about 1:1000, from about 500:1 to about 1:500, from about 200:1 to about 1:200, from about 100:1 to about 1:100, from about 50:1 to about 1:50, from about 20:1 to about 1:20, from about 10:1 to about 1:10, and/or from about 5:1 to about 1:5.

As discussed above, the compositions can further include a photoinitiator, such as a cationic photoinitiator. Examples of suitable photoinitiators include antimony-containing cationic photoinitiator, such as a triarylsulfonium hexafluoroantimonate salt (e.g., mixed triarylsulfonium hexafluoroantimonate salt in propylene carbonate, available from Dow Chemical Company).

The aforementioned compounds of the present invention (i.e., those having the formula Q-L-Z and those of Formula I) can be used in a method for preparing polymers produced by photopolymerization, and the present invention, in another aspect thereof, relates to polymers produced by such a polymerization process. For example, the compounds of the present invention having the formula Q-L-Z or the compounds of the present invention of Formula I can be formulated into a composition, as described above, and photopolymerized, as discussed in more detail below.

The aforementioned coating compositions (e.g., containing a compound of the present invention having the formula Q-L-Z, a polyol, and optional photoinitiator and other optional components or containing a compound of the present invention of Formula I, a difunctional oxetane/oxirane resin, and optional photoinitiator and other optional components) can be used in a method for preparing polymers, and the present invention, in another aspect thereof, relates to polymers produced by such a polymerization process. The method includes providing such a composition and exposing the composition to electromagnetic radiation under conditions effective to polymerize the composition. Prior to polymerization, the coating formulation can be cast into a film by a variety of techniques, including spraying, brushing, spin casting, or through the use of a Doctor blade or similar applicator. The thickness of the film can be from about 1 micron to about 250 microns, such as from about 1 micron to about 5 microns, from about 2 microns to about 4 microns, from about 1 micron to about 10 microns, from about 2 microns to about 10 microns, about 2 microns, from about 3 microns to about 4 microns, about 3.5 microns, from about 2 microns to about 200 microns, from about 10 microns to about 190 microns, from about 50 microns to about 180 microns, about 90 microns, about 100 microns, about 110 microns, about 120 microns, and/or about 130 microns.

Polymers produced in accordance with the above-described method (e.g., photopolymerization of a composition containing a compound of the present invention having the formula Q-L-Z, a polyol, and optional photoinitiator and other optional components or photopolymerization of a composition containing a compound of the present invention of Formula I, a difunctional oxetane/oxirane resin, and optional photoinitiator and other optional components) can be used to prepare electronic devices, and the present invention, in yet another aspect thereof, relates to such electronic devices.

More particularly, such electronic devices of the present invention include an electronic chip that has at least one substantially planar surface and a polymeric coating disposed on the electronic chip's substantially planar surface, where the polymeric coating includes a polymer prepared by photopolymerization of a composition containing a compound of the present invention having the formula Q-L-Z, a polyol, and optional photoinitiator and other optional components or by photopolymerization of a composition containing a compound of the present invention of Formula I, a difunctional oxetane/oxirane resin, and optional photoinitiator and other optional components. The electronic device may include other electronic components, such as resistors, capacitors, transistors, diodes, integrated circuits or other electronic chips, and power supplies. Where the electronic device includes other electronic components, these other electronic components can either be coated with a polymeric coating as described above or not.

The electronic device can further include a hole disposed through the polymeric coating and a signal transmitting element (e.g., a wire, solder ball, or other electrically conductive element; an optical waveguide or other an optically conductive element; etc.) disposed through the hole and connected (e.g., by solder, by an suitable adhesive, such as a conducting epoxy adhesive, etc.) to the electronic chip. It will be appreciated that "a hole", as used herein, is meant to refer to one or more holes, and that "a signal transmitting element", as used herein, is meant to refer to one or more signal transmitting elements (which can be of the same type or different types). The aforementioned hole (or holes) can be conveniently formed by laser ablation, for example by using a laser having a UV output, such as a UV output of from about 300 nm to about 400 nm, from about 310 nm to about 390 nm, from about 320 nm to about 380 nm, from about 330 nm to about 370 nm, and/or from about 340 nm to about 360 nm. Illustratively, a solid tripled pulsed YAG laser having an output of 355 nm can be employed. The number of pulses can be adjusted to ablate the polymeric coating to the desired depth. For example, where the polymeric coating is disposed on the surface of an electronic chip, the depth of ablation is usually equal to the thickness of the coating.

The aforementioned compositions of the present invention containing a compound of the present invention having the formula Q-L-Z, a polyol, and optional photoinitiator and other optional components or the aforementioned compositions of the present invention containing a compound of the present invention of Formula I, a difunctional oxetane/oxirane resin, and optional photoinitiator and other optional components can also be used in a method for producing a laser-ablatable film on a surface of a substrate. The method includes coating the substrate with a coating formulation of the present invention and polymerizing the coating formulation. Suitable substrates include one or more surfaces of electronic chips; suitable methods for coating the substrate with the coating formulation include those described above in regard to coating electronic chips; and suitable methods for polymerizing the coating formulation include those described above in regard to coating electronic chips.

The aforementioned compositions of the present invention containing a compound of the present invention having the formula Q-L-Z, a polyol, and optional photoinitiator and other optional components or the aforementioned compositions of the present invention containing a compound of the present invention of Formula I, a difunctional oxetane/oxirane resin, and optional photoinitiator and other optional components can also be used in a method for producing a pre-selected pattern on a surface of a substrate. The method includes producing a laser-ablatable film on a surface of a substrate in accordance with a method according to the present invention and exposing the film to ultraviolet electromagnetic radiation under conditions effective to ablate a portion of the film to produce the pre-selected pattern. The preselected pattern can be a hole or a plurality of holes arranged in a particular fashion, for example, so as to permit wires, solder balls, or other signal transmitting elements to be connected with the substrate at particular locations. Alternatively, the preselected pattern can be a pattern of ridges and valleys, where the valleys can (but need not) be of a depth which exposes the substrate. Still alternatively, the preselected pattern can be a relief similar to relief wood carving but where the medium is not wood but, instead, the laser-ablatable film.

As will be evident from the above discussion, the aforementioned compounds of the present invention having the formula Q-L-Z and the aforementioned compounds of the present invention of Formula I, as well as the compositions, polymers, and methods of the present invention containing such compounds, can be advantageously employed in the production of electronic chips by providing a method for readily forming holes, vias, or other openings in a photopolymerized packaging layer for receiving conductive elements, such as solder balls. Examples of methods for making electronic chips in which these compounds, compositions, polymers, and methods of the present invention can be employed include those which involve fluidic self assembly (e.g., as described in U.S. Pat. No. 6,417,025 to Gengel; U.S. Pat. No. 6,417,025 to Gengel; U.S. Pat. No. 6,566,744 to Gengel, which are hereby incorporated by reference). Still other examples of methods for making electronic chips in which these compounds, compositions, polymers, and methods of the present invention can be employed include those which are described in U.S. Pat. No. 6,816,380 to Credelle et al., which is hereby incorporated by reference.

The present invention is further illustrated by the following examples.

EXAMPLES

Example 1

Radiation Curable Polymer Films having Improved Laser Ablation Properties

A UV curable composition based on donor acceptor chemistry with enhanced laser ablation properties was obtained by the introduction of 2,6-naphthalene dicarboxylic acid in the backbone.

In general, the UV curable compositions involve unsaturated polyesters containing monomers that sensitize the resulting coating toward laser ablation. The unsaturated polyesters are synthesized by standard melt polyesterification techniques where diacids and diol monomers are esterified together to form the polyester resin. Unsaturated polyester resins require the presence of an unsaturated monomer, usually maleic anhydride or maleic acid, fumaric acid, itaconic acid, aconitic acid, mesaconic acid, citraconic acid, or dicholoromaleic acid. The polyols used can be one or more of the following: diethyleneglycol, ethylene glycol, propylene glycol, dipropylene glycol, butylene glycol, glycerol, neopentyl glycol, trimethylol propane, pentaerythritol, sorbitol, 1,6-hexanediol, 1,4-cyclo-hexanemethanol, and 1,2-bis(hydroxyethyl)cyclohexane.

In addition, in accordance with certain aspects of the present invention, a monomer yielding enhanced sensitivity to laser ablation is included. This monomer can be 2,6-naphthalene dicarboxylic acid ("2,6-NDA"). Without intending to be bound by theory, it is believed that 2,6-NDA, being as its absorption is in the UV region, would be sensitive during UV irradiation. It is expected that the coating would have maximum absorbance at the irradiation wavelength, thereby achieving an effective laser ablation.

The unsaturated polyester resins may be prepared by heating the carboxylic component and an organic polyol for about 10 to 15 hours to temperatures from 180° C. to 230° C. The water formed during esterification reaction is typically sparged off using an inert gas, like nitrogen.

Examples of catalysts that can be used in this reaction include paratoluenesulfonic acid, butylstannoic acid, dibutyl tin oxide, and stannous fluoride. The molecular weight of the polyester can range from 500 to 50,000. In a preferred embodiment, the polyester has a molecular weight in the range of from 500 to 2000.

Radiation curable compositions can include a vinyl ether component as an electron donor component that provides at least two vinyl ether groups per molecule of the ether component. They are also known as reactive diluents. Such products are commercially available.

In a typical embodiment, the unsaturated polyester and the reactive diluent are mixed together. Photoinitiator is added to this composition, and the resulting composition is exposed to UV irradiation to form a film.

A comparative example of a polyester without NDA was prepared by reacting 0.266 moles of triethylene glycol, 0.550 moles of 1,6-hexanediol, 0.120 moles of isophthatic acid, and 0.551 moles of maleic anhydride. Triphenyl phosphite and butyl stannoic acid was 0.1 of the total weight of the monomers. The polyesterification reaction was conducted at 180° C. and stopped when an acid value of 6.4 mg of KOH per 100 g of the sample was reached.

An example of a polyester with NDA was prepared by reacting 0.244 moles of triethylene glycol, 0.511 moles of 1,6-hexanediol, 0.054 moles of isophthalic acid, 0.041 moles of 2,6-NDA, and 0.611 moles of maleic anhydride. Triphenyl phosphite and butyl stannoic acid was 0.1 of the total weight of the monomers. The polyesterification reaction was conducted at 180° C. and stopped when an acid value of 5.4 mg of KOH per 100 g of the sample was reached.

An example of a coating formulation and crosslinking is set forth below. The polyester was combined with triethylene glycol divinyl ether in a ratio of 1:1 of the reacting functional groups. Four percent of Darocur 1173, which is a photoinitiator, was added to the composition, and the resulting mixture was homogenized. A coating was prepared from this homogenized mixture using an applicator with a clearance of 4 mil. The resultant film was tested for laser ablation properties, as follows.

During laser ablation, four by four arrays of holes were laser drilled into the coating at pulse repetitions of 1, 2, 4, 8, 16, and 32 using an advanced solid tripled YAG laser at a wavelength of 335 nm. The laser drilled samples were analyzed for (a) cleanness of ablation using an optical microscope and (b) the depth of the drilled holes using the profilometer.

Since it was found that, at higher repetition rates (16, 32), through holes were drilled in both coatings, these settings were considered too severe for any meaningful analysis. Therefore, the height/depth data was obtained and analyzed for the coatings at repetitions of 1, 4, and 8. A striking observation was that the coating containing 2,6-NDA appeared to be drilled better both in terms of hole depth and also in terms of cleanliness when observed under an optical microscope.

Table 1 contains the data for hole depths for different coatings. For this study Kapton film (polyimide) was used as the control.

TABLE 1

| Coating | Substrate thickness (microns) | Film thickness (microns) | Depth of hole 1 rep (microns) | Depth of hole 4 rep (microns) | Depth of hole 8 rep (microns) |
| --- | --- | --- | --- | --- | --- |
| polyester without 2,6-NDA | 168.6 | 2.11 | 1.315 | 4 | drilled thru |

TABLE 1-continued

| Coating | Substrate thickness (microns) | Film thickness (microns) | Depth of hole 1 rep (microns) | Depth of hole 4 rep (microns) | Depth of hole 8 rep (microns) |
| --- | --- | --- | --- | --- | --- |
| polyester with 2,6-NDA | 128.83 | 3.5 | 3.65 | 30.35 | 75.75 |
| Kapton | 75 | | 7.7 | 61.7 | 61.27 |

The optical microscope analysis also showed that cleaner ablation was obtained in case of the coating based on polyester with 2,6-NDA.

The copolyesters set forth in the following Table 2A were also prepared, and they were then crosslinked using the divinyl ether and photoinitiator described above in this Example 1. Note that, in Table 2A, the following abbreviations are used: 1,4-cyclohexanedimethanol ("CHDM"); 1,4-cyclohexanedicarboxylic acid ("CHDA"); diethylene glycol ("DEG"); 1,6-hexanediol ("1,6-HD"); isophthalic acid ("IPA"); maleic anhydride ("MA"); 2,4-naphthalene dicarboxylic acid ("2,4-NDA"); neopentyl glycol ("NPG"); propylene glycol ("PG"); triethylene glycol ("TEG"); and trimethylolpropane ("TMP").

TABLE 2A

| Sample | Copolyester components |
| --- | --- |
| UPE8R-1 | NPG, IPA, DEG, MA |
| UPE9R-1 | CHDM, DEG, adipic acid, IPA, MA |
| UPE12-5 | DEG, PG, IPA, MA |
| UPE13-13 | 1,6-HD, TEG, IPA, MA |
| UPE14-3 | 1,6-HD, NPG, TEG, IPA, MA |
| UPE15-5 | 1,6-HD, NPG, TEG, CHDA, MA |
| UPE16-1 | DEG, 1,6-HD, CHDA, MA |
| UPE17-1 | TMP, 1,6-HD, CHDA, MA |
| UPE18-1 | 1,6-HD, MA |
| UPE19-1 | TEG, 1,6-HD, IPA, MA |
| UPE20-1 | DEG, NPG, IPA, MA |
| UPE22-1 | 1,6-HD, CHDM, 2-ethylhexanoic acid, MA |
| UPE23-1 | TEG, 2-ethylhexanol, CHDA, MA |
| UPE24-1 | TEG, 1,6-HD, IPA, 2,4-NDA, MA |

Laser ablation data for crosslinked UPE8R1, UPE9R-1, UPE13-13, UPE14-3, UPE15-5, UPE16-1, UPE17-1, UPE18-1, UPE19-1, UPE20-1, UPE22-1, UPE23-1, and UPE24-1, along with laser ablation data for crosslinked Kapton and PET are presented in the following Table 2B.

TABLE 2B

| Sample | Substrate thickness (microns) | Film thickness (microns) | Depth of 1st hole (microns) | Depth of 4th hole (microns) | Depth of 8th hole (microns) |
| --- | --- | --- | --- | --- | --- |
| UPE8R-1 | 127.83 | 4.88 | 1.53 | 19.7 | 63.95 |
| UPE9R-1 | 177.5 | 12.5 | 6.2 | 20.05 | 66.1 |
| UPE13-13 | 168.6 | 2.11 | 1.315 | 4 | drilled thru |
| UPE14-3 | 124.4 | 2.76 | 3.15 | 13.75 | 41 |
| UPE15-5 | 171.2 | 7.94 | 2.65 | 24.8 | 69.9 |
| UPE16-1 | 172 | 3.166 | 2.15 | 18.45 | 63.35 |
| UPE17-1 | 175.4 | 24.31 | not drilled | 24.55 | 73.2 |
| UPE18-1 | 174.6 | 1.97 | 0.652 | 16.35 | 64.4 |
| UPE19-1 | 174 | 6.14 | 1.125 | 18.3 | 65 |
| UPE20-1 | 176 | 20 | not drilled | 0.9 | 65 |
| UPE22-1 | 176.6 | 10.8 | 5.9 | 10.6 | drilled thru |
| UPE23-1 | 175.4 | 9.76 | 1.262 | 18.55 | 70.4 |
| UPE24-1 | 128.83 | 3.5 | 3.65 | 30.35 | 75.75 |
| Kapton | 75 | | 7.7 | 61.7 | 61.27 |
| PET | 163.4 | | 8.25 | 27.65 | 20.2 |

Example 2

Study of Cationic UV Curing and UV Laser Ablation Behavior of Coatings Sensitized by Novel Sensitizers Cycloaliphatic epoxide based cationic UV curable coatings offer the advantage of fast cure, low shrinkage rate, no oxygen inhibition (Sangermano et al., *J. Mater. Sci.*, 37(22): 4753-4757 (2002) ("Sangermano"), which is hereby incorporated by reference), and good electrical properties (Koleske et al., UV-Cured Cycloaliphatic Epoxide Coatings, *National SAMPE Technical Conference*, 14:249-256 (1982) ("Koleske I"); Koleske et al., Technology of Cationic UV-Cured Cycloaliphatic Epoxide, *National SAMPE Technical Conference*, 16:529-536 (1984) ("Koleske II"); and Holland et al., Destructible Electrical Laminates, *Annu. Tech. Conf., Soc. Plast. Eng.*, Tech. Pap., 27th, 15:84-89 (1969), which are hereby incorporated by reference), and these characteristics make them ideal for microelectronic packaging applications. Polynuclear aromatic compounds are reported to be photosensitizers for onium salt cationic UV initiators to improve UV curing rate and monomer conversion (Crivello et al., *Chem. Mater.*, 14:4858-4866 (2002) ("Crivello I"); Nelson et al., *Polymeric Materials Science and Engineering*, 69:363-364 (1993); Cho et al., *Polymer Testing*, 22:633-645 (2003), and Hua et al., *Chem. Mater.*, 14:2369-2377 (2002) ("Hua"), which are hereby incorporated by reference), the sensitization is based on complex formation and electron transfer between the sensitizer and the photoinitiator (Crivello I; and Hua, which are hereby incorporated by reference). Laser ablation is becoming more and more important as a material processing tool in micromachining field (Nuyken et al., *Acta Polym.*, 49:427-432 (1998) ("Nuyken"); Kunz et al., *Appl. Phys. A*, 67:347-352 (1998) ("Kunz"); and Ortelli et al., *Macromolecules*, 33:5090-5097 (2000) ("Ortelli"), which are hereby incorporated by reference). Many materials, such as polyimide, polycarbonate, and PMMA, have been studied for laser ablation behavior (Kunz; Ortelli; and Wee et al., *Bull. Korean Chem. Soc.*, 22(8):914-916 (2001) ("Wee"), which are hereby incorporated by reference). The addition of dopant, such as pyrene or naphthalene, is a common practice in aiding laser ablation (Wang et al., Etching of Transparent Materials by Laser Ablation of an Organic Solution. *RIKEN Review*, 32:Focused on Laser Precision Microfabrication (LPM2000) (2001), which is hereby incorporated by reference). The mechanism of laser ablation has been widely studied, and both pyrolysis and photolysis are found to be involved (Nuyken; Ortelli; Wee; and Lippert, *Adv. Polym. Sci.*, 168:51-246 (2004) ("Lippert I"), which are hereby incorporated by reference), but which mechanism is predominant depends on both laser source and material used (Lippert I; Lippert et al., *Appl. Phys. A*, 77:259-264 (2003), which are hereby incorporated by reference). At the beginning of ablation, a stage called incubation is commonly observed during which the less absorbent material is turned into a more absorbent intermediate upon the energy delivered by incident laser light (Kunz; and Ortelli, which are hereby incorporated by reference). In a specific microelectronic packaging step of Alien Technology Company, a cycloaliphatic epoxide based cationic UV curable coating is proposed to be applied onto polysulfone substrate then cured by UV light and ablated by 355 nm YAG laser to create through holes on coating film. Since the cost of each photon is of most concern in laser processing (Lippert I, which is hereby incorporated by reference), it is desired to reach the designated via dimension with the least number of laser photons. Also, debris in the ablation spot and surrounding area should be minimized. To our best knowledge, no research has been done on laser ablatable cationic UV curable coating. It was found earlier by our group that the addition of monomeric pyrene into cycloaliphatic epoxide/difunctional oxetane/sulfonium salt based cationic UV curable coating greatly enhanced the coating's laser ablation depth, but the curing time doubled from 30 seconds to 60 seconds. The deterred curing was attributed to the incompatibility between monomeric pyrene and the host coating. It was hypothesized that, due to this incompatibility, the UV energy absorbed by pyrene cannot be utilized to sensitize the photoinitiator since the chance of complex formation between pyrene and photoinitiator is much less. As a result, the net UV energy that reaches photoinitiator is reduced, consequently causing slower curing of the coating. A solution to above dilemma is an additive that enhances laser ablation without deterring UV curing, and this challenge is addressed in this work.

More particularly, with the intention to improve their compatibility, novel sensitizers were synthesized based on reaction between naphthalene or anthracene derivatives and ingredients (cycloaliphatic epoxide, oxetane and polyol) in the coating. The syntheses and characterization of the resulting materials are discussed below in Examples 3-9. Briefly, HPLC and GC-MS confirmed the formation of desired sensitizers. Three coating systems based on cycloaliphatic epoxide and oxetane or polyol were formulated with the reactive sensitizers. Sensitized coatings exhibited faster cationic UV curing and better UV laser ablation performance, coatings with anthracene based sensitizer even have better ablation performance than Kapton. Sensitized coatings have higher hardness, Tg and crosslink density than the original coatings. No adverse effect was observed on the coating's adhesion and solvent resistance after sensitizer addition. The relationship between coating's Tg and laser ablation behavior was investigated, and this investigation revealed that the higher the Tg and crosslink density, the worse the ablation.

Example 3

Experimental Details Regarding the Synthesis and Characterization of Reactive Sensitizers The following materials were used in the experiments. Cyracure™ UVR 6110 difunctional cycloaliphatic epoxide (3,4-epoxycyclohexylmethyl-3,4-epoxycyclohexane carboxylate, "ECC"); UVR 6000 mono-functional reactive oxetane diluent (3-ethyl-3-hydroxy-methyl oxetane, "EHMO"); TONE™ 0301 (ε-caprolactone polyol, "PCL") flexibilizer; and UVI 6974 photoinitiator (mixed triarylsulfonium hexafluoroantimonate salt in propylene carbonate, "PI") were obtained from Dow Chemical Company. Difunctional oxetane reactive diluent OXT-221 (bis([1-ethyl(3-oxetanyl)]methyl)ether, "DOX") was provided by Toagosei Co., Ltd. AMBERLYST® 15 ion-exchange resin with sulfonic acid functionality (A15), AMBERLYST® A-21 ion-exchange resin with alkyl tertiary amine functionality ("A21"), naphthalene dicarboxylate ("NDC"), and 9-anthracene carboxylic acid ("ACA") were obtained from Aldrich. All materials were used as received.

Figure 1B:
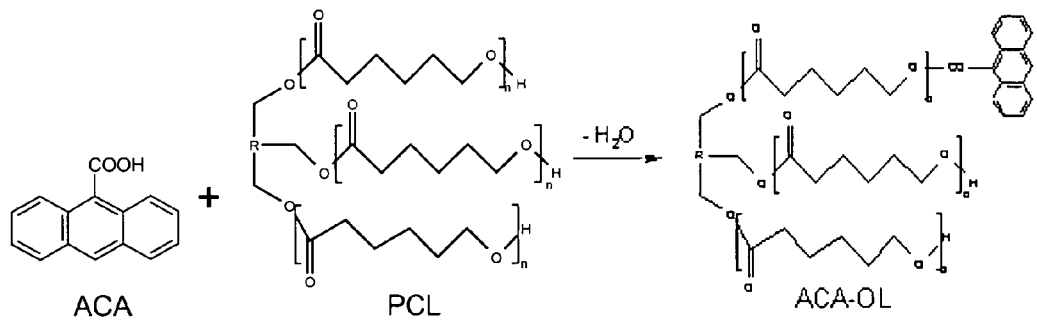
Figure 1C:
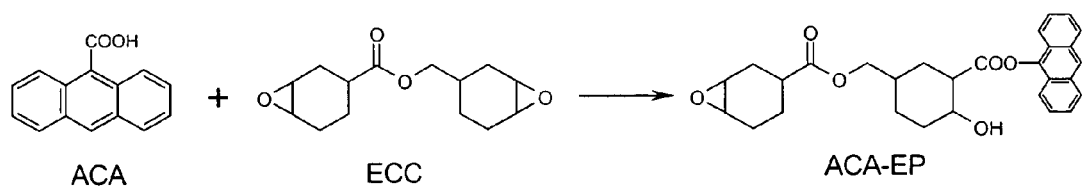

The novel reactive sensitizers were synthesized using the synthetic routes described in FIG. 1. Syntheses were carried out in a 100 ml three-neck flask equipped with nitrogen inlet, reflux condenser, and magnetic stirrer. The reaction temperature was maintained by a heating mantle and a thermocouple linked to a temperature controller. Reaction mixture was dried in vacuum oven (30 mm Hg, 65° C.) before characterization and use.

The transesterification reaction of NDC and EHMO was accomplished by adding 6.11 g NDC, 5.80 g EHMO (mole ratio=1:2), 1.77 g A21, and 30 g xylene to the reaction flask. The mixture was heated and kept at 100° C. for 24 hours with nitrogen purge. The product is abbreviated as NDC-OX.

The esterification reaction of ACA and PCL was accomplished by adding 1.11 g ACA, 1.50 g PCL (mole ratio=1:1), 0.1 g A15, and 20 g xylene to the reaction flask. The mixture was heated and kept at 120° C. for 29 hours with nitrogen purge. The product is abbreviated as ACA-OL.

The epoxide ring opening reaction of ECC by ACA was accomplished by adding 0.63 g ACA, 0.56 g ECC (mole ratio=1:1), and 20 g xylene to the reaction flask. The mixture was heated and kept at 120° C. for 18 hours. The product is abbreviated as ACA-EP.

The synthesized reactive sensitizers were characterized as follows.

High performance liquid chromatography ("HPLC") analysis was performed on an Agilent 1100 series HPLC utilizing the diode array detector ("DAD") for UV/Vis characterization. Chromatographic separation was achieved on a reversed-phase ZORBAX C8 column (from Agilent) with a C4 guard column (from Thermo Electron). The mobile phase consisted of two solvents: Solvent A (0.05 M ammonium phosphate, pH unadjusted) and solvent B (methanol). Column temperature was maintained at 40° C. throughout the analysis. A 15 μl injection volume was used for all samples. The column was eluted with the following gradient: 0 min, 35% B; 18 min, 35% B; 18.1 min, 85% B; 28 min, 85% B; 28.1 min, 35% B. Flow rate was 0.7 ml/min with a 40 minute runtime per injection.

GC-MS analysis was performed on HP 6890 gas chromatography and HP 5973 mass selective detector utilizing EI (electron ionization) with filament energy of 69.9 kev. Initial GC oven temperature was 70° C.; then it was ramped up to 300° C. at a rate of 20° C./min. The front inlet was in split mode with inlet temperature 250° C. and pressure 8.24 psi. The split ratio and the run time (normally 1 hour) varied with different samples. Separation was achieved on a ZEBRON ZB-35 capillary column operated in a constant flow mode with flow rate of 1.0 ml/min and with an average velocity of 36 cm/s. The mass spectrometer was in scan mode with m/z ranges from 10 to 800, and the temperature for MS source and MS Quad were set at 230° C. and 150° C. respectively.

Coating films were prepared by casting the liquid sample onto an aluminum panel or a polysulfone film (thickness ~130 μm) with a Gardco 70# wire drawdown bar. The cured coating film generated has a thickness of 90-120 μm, which is much thicker than normal thickness of UV coatings (10-20 μm). With such unusually thick films, it was possible to obtain more data to better describe how the laser ablation progresses in the coating film as the pulses increases. A problem that accompanies thicker coating film is the curling on the polysulfone substrate, especially for 3.8 and 3.9 systems due to internal stress generated during UV curing. However, when the cured film thickness was reduced to around 20 μm, a flat film is achieved.

UV curing of coating samples was performed using a Dymax light source with a 200 EC silver lamp (UV-A, 365 nm). The intensity was 35 mW/cm² measured by NIST Traceable Radiometer, International Light model IL1400A. The curing was performed in air. Cured film thickness was measured using a MICROMASTER® micrometer.

Photoinfrared experiments were performed using a Nicolet Magna-IR 850 spectrometer series II with detector type DTGS KBr, and a UV optic fiber mounted in a sample chamber which humidity is kept constant at around 20% by DRIERITE®. The light source was a LESCO Super Spot MK II 100W DC mercury vapor short-arc lamp. Such a setup monitors the functional group conversion as the reaction proceeds and is known as real-time infrared spectrometry ("RTIR"). Coating samples were spin coated onto a KBr plate at 3000 rpm for about 15 s. The coating sample was then exposed to UV light for 60 s, and scans were taken over a 120 s period at a scan rate of 1 scan/second. The UV source was adjusted to about 3.6 mW/cm², and the experiment was performed in air. The cycloaliphatic epoxide conversion of ECC was monitored at 789 cm$^{-1}$, and the oxetane conversion of EHMO and DOX was monitored at 976 cm$^{-1}$.

Differential scanning calorimetry ("DSC") was performed on a TA Instruments Q1000 series calorimeter. Samples were subjected to a heat-cool-heat cycle from −50° C. to 200° C. at a ramp rate of 10° C./min. Tg values were determined as the midpoint of the inflection from the second heat cycle. Dynamic mechanical thermal analysis ("DMTA") was performed using a Rheometric Scientific 3E apparatus in the rectangular tension/compression geometry. Free film of the cured coating was obtained on polysulfone substrate using razor blade. Sample size for testing was 10 mm×5 mm. The analysis was carried out from 0 to 250° C. at a frequency of 10 rad/s and a ramp rate of 5° C./min. Tg was obtained from the maximum peak in the tan δ curves. Crosslink density ($v_e$) is calculated according to equation: $E'=3v_eRT$, where the E' value was determined in the linear portion at least 50° C. greater than the Tg.

Hardness testing was performed with a BYK Gardener pendulum hardness tester in the König mode on an aluminum panel.

Cross-hatch adhesion test was performed on polysulfone substrate using a Gardco cross-hatch cutter which creates a 5×5 squares pattern; adhesive tape was then applied onto the pattern; and the adhesive tape was pulled off to examine coating loss.

Methyl ethyl ketone ("MEK") double rub experiment was used to assess the coating's solvent resistance. Coating samples were applied onto aluminum panels, UV cured, and placed at room temperature for 1 hour before test. A 26-ounce hammer with 5 layers of cheesecloth wrapped around the hammerhead was soaked in MEK for rubbing. After 100 double rubs, the cloth was rewet with MEK. The number of double rubs was reported once mar appeared on the film surface.

Figure 2:
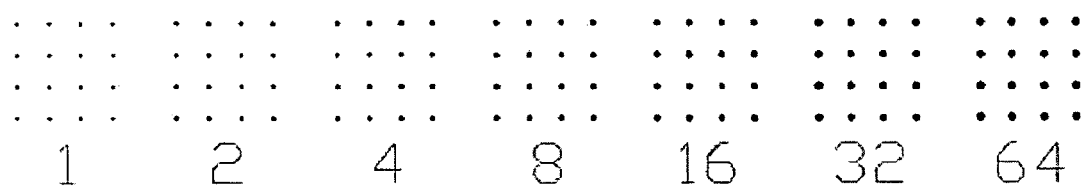
FIG. 2 is a schematic representation of via arrays created by 355 nm YAG laser ablation of a coating produced with a coating formulation in accordance with the present invention.

UV laser ablation of cured coating films on polysulfone substrate was carried out using YAG laser. Laser parameters were: wavelength 355 nm, power 0.2 W, effective laser beam spot size 40 μm, beam spiral diameter 200 μm, velocity 125 mm/s, repetition rate 20 kHz. For each sample film, a 16-via array was generated (as shown in FIG. 2. Nitrogen flow over the film surface was used to blow away ablation debris.

Wyko NT3300 Optical Profiler from VEECO was used to obtain profile data of vias created by laser ablation. VSI (vertical scanning interferometry) mode, which is suitable for relatively rough surfaces, and a magnification of 50×0.5 were used. Back scan length was set at 20 μm, and scan length was varied from 100 to 250 μm as pulses increased. Vision 32 for NT-2000 software, version 2.303, was used to process the profiler data. Only the center four vias were selected for measurement. UV-Vis spectra of the coating film was achieved on a Varian Cary 5000 UV-Vis-NIR spectrophotometer operating in the absorption mode. The scanning rate was 600 nm/min, and scanning range was 200-600 nm. The coating was applied and UV cured on a quartz slide with film thickness between 20-24 μm. The cationic UV curable coating formulations studied in this work are set forth in Tables 3A-3C.

TABLE 3A

| Sample | 3.8-1 | 3.8-2 | 3.8-3 | 3.8-4 | 3.8-41 | 3.8-5 | 3.8-51 |
|---|---|---|---|---|---|---|---|
| ECC (wt %) | 70 | 70 | 70 | 70 | 70 | 70 | 70 |
| EHMO (wt %) | 25 | 25 | 25 | 15 | 15 | 5 | 5 |
| DOX (wt %) | 0 | 0 | 0 | 10 | 10 | 20 | 20 |
| PI (wt %) | 4 | 4 | 4 | 4 | 4 | 4 | 4 |
| NDC-OX (mmol/5 g) | 0 | 0.1 | 8 | 0 | 0.1 | 0 | 0.1 |
| ACA-OL (mmol/5 g) | 0 | 0 | 0.1 | 0 | 0 | 0 | 0 |

TABLE 3B

| Sample | 3.9-1 | 3.9-2 | 3.9-3 |
|---|---|---|---|
| ECC (wt %) | 70 | 70 | 70 |
| DOX (wt %) | 25 | 25 | 25 |
| PI (wt %) | 4 | 4 | 4 |
| NDC-OX (mmol/5 g) | 0 | 0.1 | 0 |
| ACA-OL (mmol/5 g) | 0 | 0 | 0.1 |

TABLE 3C

| Sample | 3.10-1 | 3.10-2 | 3.10-3 | 3.10-4 | 3.10-5 |
|---|---|---|---|---|---|
| ECC (wt %) | 70 | 70 | 70 | 80 | 90 |
| PCL (wt %) | 25 | 25 | 25 | 15 | 5 |
| PI (wt %) | 4 | 4 | 4 | 4 | 4 |
| NDC-OX (mmol/5 g) | 0 | 0.1 | 0 | 0 | 0 |
| ACA-OL (mmol/5 g) | 0 | 0 | 0.1 | 0 | 0 |

Example 4

Results Regarding the Synthesis and Characterization and Effects of Reactive Sensitizers—Effect of Non-Modified Sensitizers It is believed that material's absorption of incident laser energy is of most importance for a successful laser ablation (Nuyken; and Lippert I, which are hereby incorporated by reference). Since we chose to work with UV lasers having a wavelength of 355 nm, we focused on naphthalene and anthracene derivatives instead of pyrene in this work due to their stronger absorption around 355 nm (Ouchi et al., *J. Appl. Polym. Sci.*, 20:1983-1987 (1976) ("Ouchi"); and Kasapoglu et al., *Macromol. Rapid Commun.*, 23:567-570 (2002), which are hereby incorporated by reference). Addition of 0.0222 g (0.1 mmol) ACA into 5 g of 3.8-1 and 3.10-1 (formulas were named 3.8-ACA, 3.10-ACA respectively) was tried. It was thought that ACA, as an acid and proton donor, could help in the photo-induced super acid generation in the initiation step (Crivello et al., In *Photosensitizations for Free Radical, Cationic and Anionic Photopolymerization,* 2nd ed., New York: John Wiley & Sons (1998), which is hereby incorporated by reference). Also, it might be incorporated into the crosslinking network as a chain transfer agent so that it would not migrate out of the cured film with time. Coating samples with ACA were heated to 50° C. for about 30 minutes to dissolve ACA (which is not a good sign for acceptable compatibility). RTIR was conducted for these samples, and Table 4 shows a comparison of functional group conversion vs. time in RTIR experiments for coatings with and without ACA. As shown in Table 2B, deterred curing (lower monomer conversion than the original coating at the same sampling time) was observed. The deterred curing was attributed to the same reason as the monomeric pyrene added coatings.

TABLE 4

| Time (s) | Epoxide conversion (%) | | Oxetane conversion (%) | | Epoxide conversion (%) | |
|---|---|---|---|---|---|---|
| | 3.8-1 | 3.8-ACA | 3.8-1 | 3.8-ACA | 3.10-1 | 3.10-ACA |
| 5 | 18 | 9 | 28 | 10 | 62 | 25 |
| 10 | 26 | 11 | 34 | 16 | 69 | 35 |
| 15 | 29 | 16 | 37 | 18 | 72 | 49 |
| 20 | 28 | 20 | 39 | 19 | 72 | 56 |
| 25 | 29 | 16 | 40 | 20 | 71 | 65 |
| 30 | 32 | 18 | 41 | 23 | 73 | 64 |
| 60 | 32 | 24 | 44 | 25 | 77 | 68 |
| 90 | 32 | 23 | 44 | 24 | 79 | 68 |
| 120 | 34 | 23 | 45 | 26 | 77 | 69 |

Example 5

Results Regarding the Synthesis and Characterization and Effects of Reactive Sensitizers—Synthesis and Characterization of Reactive Sensitizers It seemed that good compatibility is the key to effective sensitization. Modification of monomeric polynuclear aromatic sensitizers is an effective way to enhance their solubility in the coating and lower their vapor pressure and toxicity (Crivello I, which is hereby incorporated by reference). A direct way to achieve good compatibility would be the attachment of the polynuclear aromatic compounds to the coating ingredients, such as epoxide resin and reactive diluents. An added advantage of such modification is that these reactive ingredients will secure the binding of polynuclear aromatic compounds to the crosslinked coating network, thus ensuring a stable film property since any potential sensitizer migration would then be inhibited. Based on this thought, three reactive sensitizers were synthesized as described in Example 3. The formation of the three reactive sensitizers was confirmed by HPLC and GC-MS as described below.

The NDC-OX is a white powder soluble in acetone and chloroform. The formation of NDC-OX was confirmed by GC-MS. Peaks at 5.51 and 12.45 min in the GC chromatogram were attributed to unreacted EHMO and NDC respectively, and a peak at 16.19 min was attributed to NDC-OX (MW 328). In the MS chromatogram of GC's NDC-OX peak, its molecular ion (m/z=328) was observed. The reaction product mixture contained about 71.8% NDC-OX.

The ACA-EP is a brownish viscous liquid. In the GC chromatogram, peaks at around 11, 1,2 and 14 minutes were attributed to ECC, and a peak at 13.86 minutes was attributed to ACA. Four peaks at between 25 to 29 minutes were attributed to ACA-EP (MW 474). All have similar MS chromatograms with m/z peaks at 177, 205 and 222. These peaks are the characteristic fragments of ACA, which indicates the presence of ACA in the synthesized product. Due to the asymmetry of ECC, the ACA can attack either of the two epoxide rings to form two structurally different products. It was concluded that the attack to the ring closer to the carbonyl of ECC is predominant based on the following reasoning: (i)

if the cleavage of ACA-EP occurs on the ester group of ECC, the attachment of ACA to the closer epoxide ring would form a fragment with m/z=347, while the attachment to the other ring would form a fragment with m/z=349; (ii) since the m/z=346 peak predominates, it was concluded that the attack to the ring closer to the carbonyl of ECC is predominant. The slight structural difference of ACA-EP is not expected to affect its reactivity and other concerned properties such as UV absorbance, mobility, etc. in this work. The reaction product mixture contains about 56.2% ACA-EP.

The ACA-OL (MW 522) is a yellowish paste. GC-MS did not show any new product peaks except for the peaks of ACA and PCL. In HPLC analysis, there was indication of target product formation. The HPLC chromatogram showed two peaks at about 15 minutes, and these peaks were attributed to unreacted ACA. All the peaks in the HPLC chromatogram after 20 minutes have UV absorption spectra different from both ACA and PCL, indicating new product formation. All product peaks (except for two minor ones) have ACA's characteristic UV absorption between 330-390 nm, indicating attachment of ACA to polyol. The reaction product mixture contains about 49.5% ACA-OL.

The above synthesized products are expected to be "reactive" sensitizers since the epoxide or oxetane group in ACA-EP and NDC-OX can take part in the photopolymerization, and the polyol moiety in ACA-OL can be incorporated into the crosslink network via chain transfer reaction (Crivello et al., *J. Rad. Cur.*, 13(4):2-6, 8-9 (1986) ("Crivello II"), which is hereby incorporated by reference). Further separation/purification of the reaction product mixture was not carried out since decent amount of monomeric polyaromatic compounds had been modified according to the spectroscopic data, and the unreacted coating ingredients will still take part in photopolymerization as usual. The reaction product mixtures were put into formulation after removing the catalyst and solvent.

Example 6

Results Regarding the Synthesis and Characterization and Effects of Reactive Sensitizers—Effect of Reactive Sensitizers The reactive sensitizers were added into the UV coating formula with the ratio of 0.1 mmol/5 g coating (about 1% wt). Formulas with 0.1 mmol ACA-EP were named 3.8-ACA-EP, 3.9-ACA-EP, and 3.10-ACA-EP. The sensitizers dissolved in the coating after being heated at about 50° C. for 15 minutes on hot plate. The resultant samples are clear liquid under room temperature, indicating good compatibility. Characterizations of these sensitized coatings were carried out to examine sensitizer's effect.

Figure 3A:
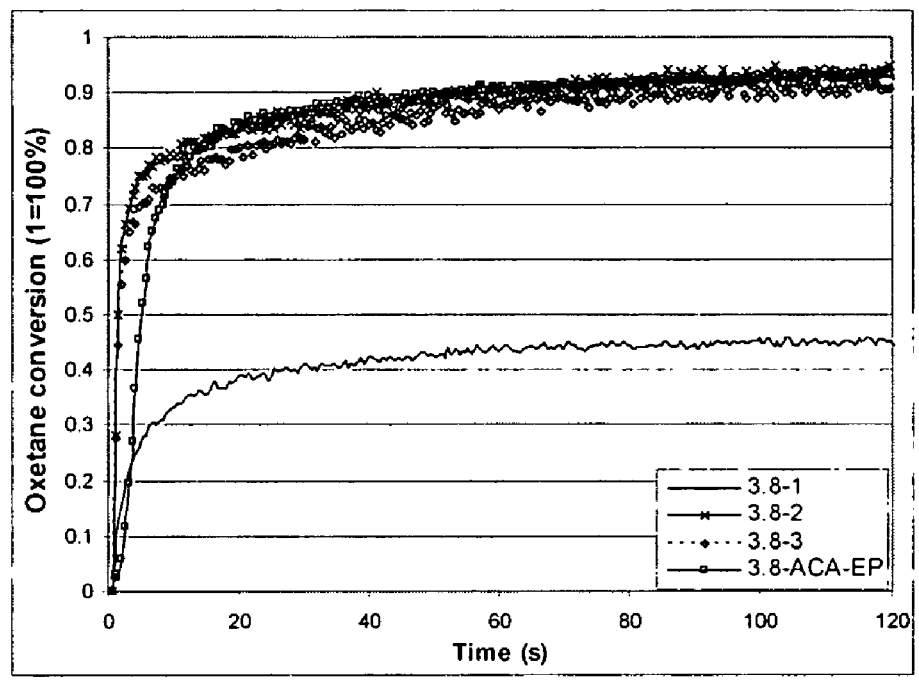
FIGS. 3A-3B are real-time infrared spectrometry ("RTIR") plots for oxetane conversion of coatings sensitized using various reactive sensitizers according to the present invention.
Figure 3B:
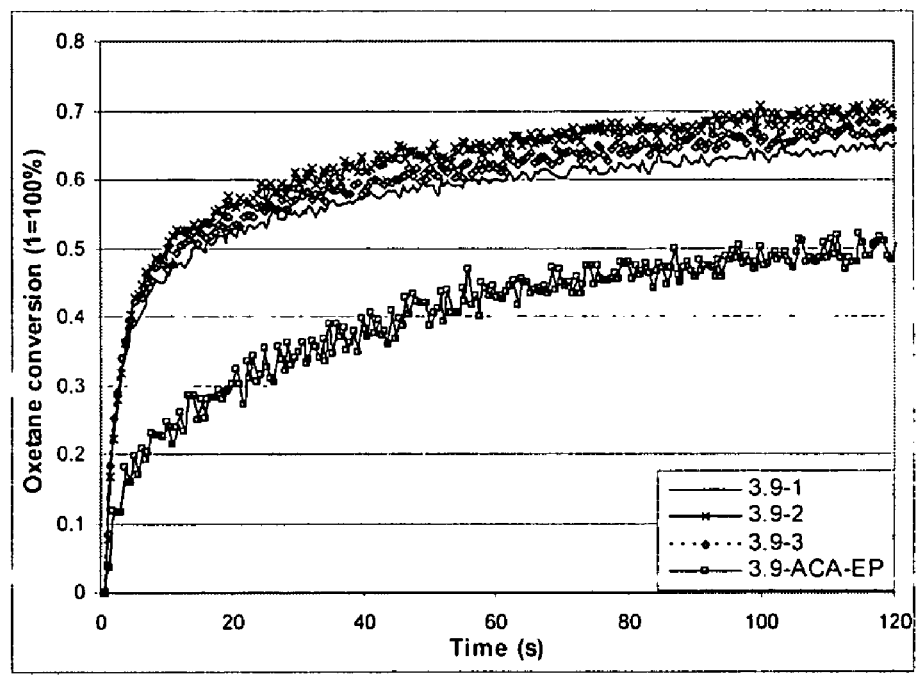

The reactive sensitizers' effect on the coating's curing behavior was studied using RTIR with comparison to the blank formula. Table 5 and FIGS. 3A and 3B show the RTIR data of different formulation systems.

TABLE 5

| Time (s) | Epoxide conversion (%) | | | | | | | | | | | |
|---|---|---|---|---|---|---|---|---|---|---|---|---|
| | 3.8-1 | 3.8-2 | 3.8-3 | 3.8-ACA-EP | 3.9-1 | 3.9-2 | 3.9-3 | 3.9-ACA-EP | 3.10-1 | 3.10-2 | 3.10-3 | 3.10-ACA-EP |
| 5 | 18 | 49 | 33 | 26 | 24 | 20 | 29 | 17 | 62 | 59 | 49 | 64 |
| 10 | 26 | 54 | 39 | 37 | 27 | 26 | 36 | 18 | 69 | 66 | 62 | 71 |
| 15 | 29 | 55 | 42 | 42 | 32 | 27 | 40 | 29 | 72 | 69 | 68 | 72 |
| 20 | 28 | 54 | 47 | 50 | 35 | 29 | 35 | 23 | 72 | 71 | 69 | 76 |
| 25 | 29 | 54 | 44 | 46 | 36 | 31 | 41 | 26 | 71 | 73 | 71 | 75 |
| 30 | 32 | 59 | 44 | 52 | 40 | 32 | 37 | 28 | 73 | 74 | 73 | 77 |
| 60 | 32 | 62 | 47 | 50 | 42 | 38 | 46 | 37 | 77 | 76 | 76 | 80 |
| 90 | 32 | 63 | 51 | 53 | 45 | 42 | 50 | 36 | 79 | 80 | 77 | 82 |
| 120 | 34 | 66 | 52 | 52 | 44 | 43 | 51 | 41 | 77 | 80 | 79 | 82 |

Table 6 sets forth a comparison of thermal and mechanical properties of coatings with and without sensitizers.

TABLE 6

| | 3.8-1 | 3.8-2 | 3.8-3 | 3.9-1 | 3.9-2 | 3.9-3 | 3.10-1 | 3.10-2 | 3.10-3 |
|---|---|---|---|---|---|---|---|---|---|
| Film Thickness (μm) | 90 | 110 | 120 | 100 | 110 | 90 | 90 | 110 | 90 |
| X-hatch adhesion | | 25/25 | | | 25/25 | | | 25/25 | |
| MEK rub (cycles) | | >400, no mar | | | >400, no mar | | 50 | 100 | 50 |
| Pend. hardness (s) | 197 | 213 | 220 | | not measured | | 195 | 196 | 194 |
| Curling | | slight | | | serious | | | very slight | |
| DSC Tg (° C.) | 49.98 | 47.04 | 47.86 | 47.19 | 50.64 | 50.84 | 45.36 | 45.69 | 45.85 |
| DMTA Tg 1 (° C.) | 135.5 | 149.0 | 145.4 | 167.1 | 161.0 | 150.2 | 93.60 | 103.4 | 91.98 |
| DMTA Tg 2 (° C.) | | not observed | | | not observed | | 132.5 | 176.7 | no |
| $v_e$ (× mmol/cm$^3$) | 8.203 | 9.962 | 10.38 | 22.13 | 27.84 | 21.45 | 2.420 | 2.580 | 2.811 |

Referring to the RTIR data shown in Table 5 and FIGS. 3A and 3B, in the 3.8 coating system, all the formulations with reactive sensitizer exhibit pronounced accelerated curing (higher monomer conversion at the same sampling time) than the blank formula 3.8-1, especially in the case of oxetane conversion. In the 3.9 coating system, the acceleration effect is less pronounced; also, in the 3.9 coating system, the addition of ACA-EP deters the curing. The difference between the 3.8 and 3.9 systems can be attributed to mobility factors. In comparison to the 3.8 system, the 3.9 system is a highly crosslinked system in which the vitrification point is earlier (compared to the 3.8 system). Since an effective sensitization depends on collision, complex formation, and electron transfer between the sensitizer and initiator molecules (Crivello I, which is hereby incorporated by reference), a "rigid" system like 3.9 would "freeze" the molecules early so that the sensitization interaction is restrained. Furthermore, since cycloaliphatic epoxide is initiated easier than oxetane in UV curing process (Sasaki, pp. 61-68 In *Oxetanes: Curing Properties in Photo-cationic Polymerization*, RadTech 2000, Baltimore, Md., United States (2000) ("Sasaki"), which is hereby incorporated by reference), the sensitizer ACA-EP is bound to the network earlier than NDC-OX and ACA-OL, and, therefore, its chance to interact with the initiator is much less. Consequently, it can only act as a UV absorbent that slows down the curing. In the case of the 3.8 system, the mono functional oxetane provides enough mobility so that sensitization is effective, even when the sensitizer is bound to the network earlier, as in the case of ACA-EP. In the 3.10 system, the mobility provided by large amount of polyol is the greatest. Moreover, as a chain transfer agent, the polyol helps to boost the monomer conversion rate (Crivello II; Koleske, *Polym. Paint Colour J.*, 179(4249):796-798, 800, 802, 804 (1989) ("Koleske III"); and Goldberg et al., *Mod. Paint Coatings*, 82(12):36, 39-40, 42 (1992) ("Goldberg"), which are hereby incorporated by reference). As a result, the cycloaliphatic epoxide's conversion is already high enough that sensitizers would play fewer roles in curing process. These factors account for the slight differences of curing behavior observed in 3.10 system. The above explanation is further validated by comparing the crosslink density data of the 3.8, 3.9, and 3.10 systems, as shown in Table 6.

In order to compare the real life curing behavior, above formulas were also applied onto aluminum panels and cured using UV lamp. All the formulas can be cured after 60 s UV radiation to form a clear solid film except for the formulas containing ACA-EP, for which wrinkle was found on cured film surface. The reason for wrinkling may be the earlier initiation and polymerization of the cycloaliphatic epoxide, thus the epoxide linked ACA will be bound to crosslinked network in the early stage and act as a UV absorbent, deterring the curing of the bottom part of the coating. Formulas containing ACA-EP were not taken for further test because of the wrinkling problem.

Figure 4A:
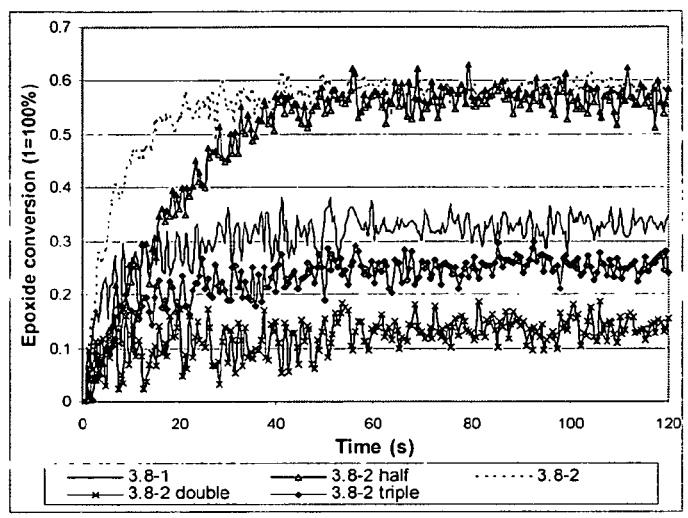
FIGS. 4A-4C are RTIR plots for oxetane conversion of coatings sensitized using various amounts of a reactive sensitizer according to the present invention.
Figure 4B:
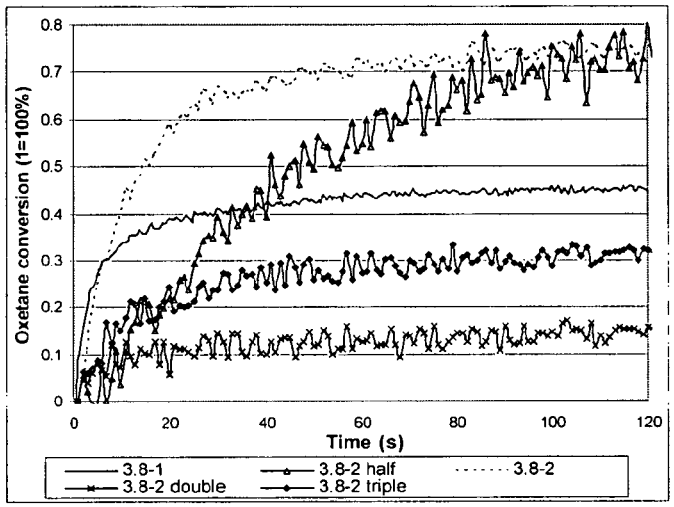
Figure 4C:
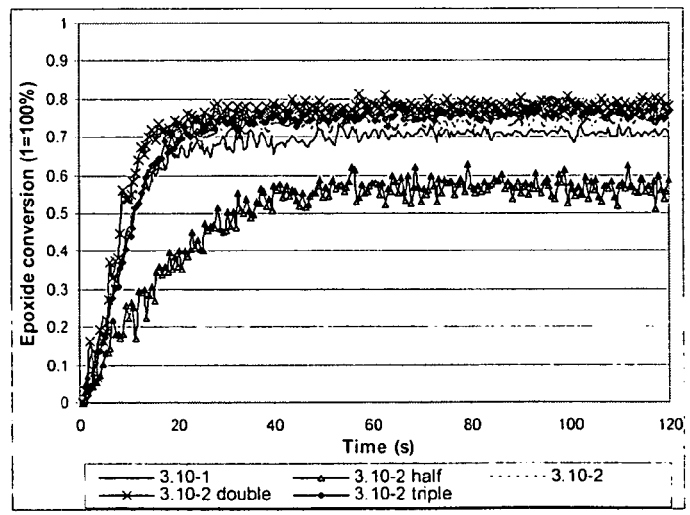

The sensitizer's amount in the coating formula was varied to see its effect on UV curing. Formulas studied were based on 3.8-2 and 3.10-2 formulations. Formulas 3.x-2 half, double, and triple represent the NDC-OX's amount is half, double, and triple of 0.1 mmol (0.0328 g)/5 g respectively. RTIR study results was shown in FIGS. 4A-4C, from which it can be seen that there exists an optimum sensitizer amount in terms of UV curing acceleration. For example, for the 3.8 system, the amount is 0.1 mmol. For the 3.10 system, the amount is 0.2 mmol.

The sensitized coatings' mechanical and thermal properties were studied together with original coatings in order to understand the sensitizer's effect. Table 6 summarizes the results. All the formulas studied exhibit excellent adhesion on polysulfone, and the 3.8 and 3.9 samples also have excellent solvent resistance. For 3.10 samples, the addition of large amount of polyol accounts for poor solvent resistance. For one, as a chain transfer agent, the polyol causes formation of lower molecular weight polymers (Ouchi; Crivello II; and Sasaki, which are hereby incorporated by reference), and, on the other hand, the residual polyol with linear structure is susceptible solvent attack. All samples' DSC glass transition is not obvious. From DMTA, we can see a general trend after addition of sensitizers, which is higher Tg and $v_e$, and this correlates well with higher monomer conversion of sensitized samples as seen in the RTIR data. For 3.8 system, the monomer conversion was increased drastically after the addition of sensitizers, and, as a result, $v_e$ and DMTA Tg are all substantially higher than the original formula. Due to improved Tg and E', the hardness was also subsequently higher. As to the 3.9 and 3.10 systems, the sensitizers' aid in converting the monomers is much less obvious, and, thus, only slight difference is observed in above properties, including hardness. The curling grading is obtained by visual inspection, and is related well with the $v_e$ data. The 3.9 system has the highest $v_e$; hence its curling is serious and the films formed are brittle, possibly reducing its potential in practical applications. One noticeable phenomenon is that almost all of the 3.10 samples exhibit two DMTA Tgs. This may be an indication of microphase separation of the cured coating.

The following describes the results of laser ablation of sensitized coating films.

Figure 5A:
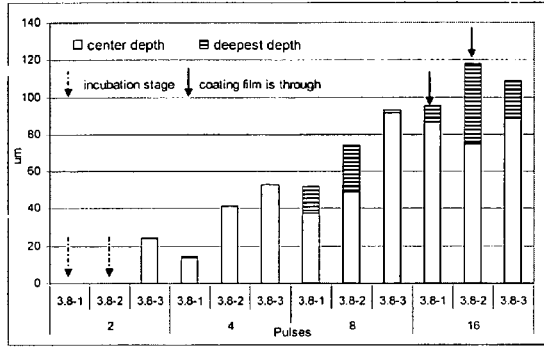
FIGS. 5A-5E are bar graphs showing the dimensions of the vias created by laser ablation of coatings produced with various coating formulations in accordance with the present invention.
Figure 5D:
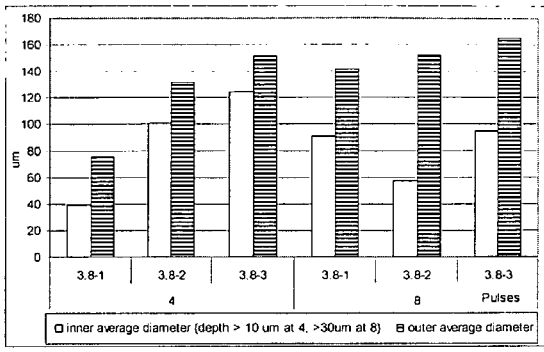
Figure 5B:
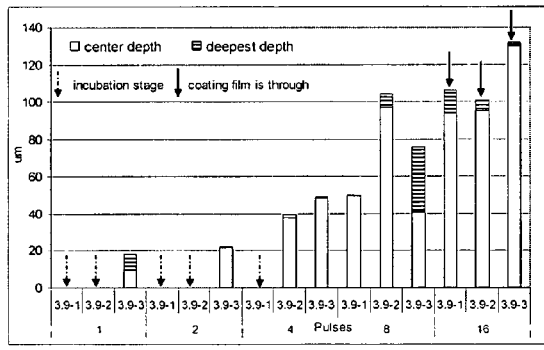
Figure 5E:
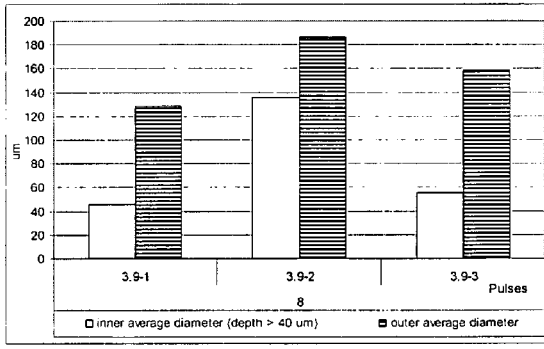
Figure 5C:
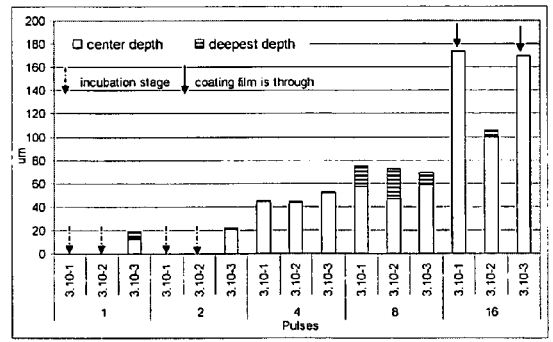
Figure 5F:
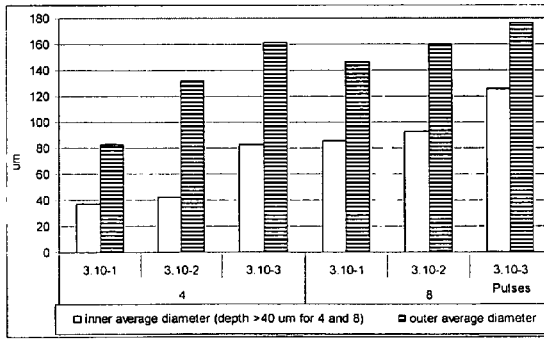

The profile data of vias created by UV laser ablation on UV cured coating films and two reference films, Kapton (polyimide) and PEN (polyethylene naphthalene), were obtained from profiler and processed in Vision 32 for NT-2000 software. Vias of the coatings films and PEN have a crater like profile with uneven bottom. Vias of Kapton are different. A cone was found in the via at all pulses, which is attributed to impurities (Lippert I, which is hereby incorporated by reference). Center depth readings were obtained and recorded. The deepest depth was obtained from a "filtered histogram" analysis chart provided by the Vision 32 software. The outer average diameter of the via was obtained by measuring and averaging the outer x and y diameter. The inner average diameter was obtained by using the "data restore" function in the "processed options" first, then by measuring and averaging the x and y diameter below certain depth. Ablated vias' dimension data are shown in FIGS. 5A-5E. In FIGS. 5A-5C, the dash line arrow indicates that the sample is still in incubation stage at that pulse (Kunz; and Ortelli, which are hereby incorporated by reference). A typical sign of incubation is the existence of a lump above the film plane. The solid line arrow in FIGS. 5A-5C indicates a through hole in the coating film at that pulse. From FIGS. 5A-5E, it is apparent to see that even addition of small amount of reactive sensitizers (about 1% in weight) greatly enhances laser ablation on the coating films. This is especially true at the initial several pulses (pulses 1, 2, and 4).

Improvement in ablation after sensitizer addition can be seen in 3 aspects.

First, ablation starts earlier. This can be observed at 1 and 2 pulses for all systems. Coatings sensitized by ACA-OL especially exhibit this characteristic.

Second, the ablation depth is deeper at the same pulse. For the 3.8 and 3.9 systems, at the pulse where all the samples begin to be ablated (pulses 4 and 8 for 3.8 and 3.9 respectively), the ablation depth for the sensitized coatings is almost double that of the blank sample and reaches 40-50 μm. Given the coating has a film thickness of 20 μm (which is normal for radiation cure coatings) the above result means the ablation on the 3.8-3 coating has already created a through-hole while ablation on other coating samples have not even started. As to the 3.10 system, the depth improvement is less which can be explained by lower polymer molecular weight and higher mobility inside the cured film caused by a large amount of the polyol (Lippert I; Sasaki; Koleske III; and Goldberg, which are hereby incorporated by reference); thus even the blank sample can be ablated easily.

Figure 6:
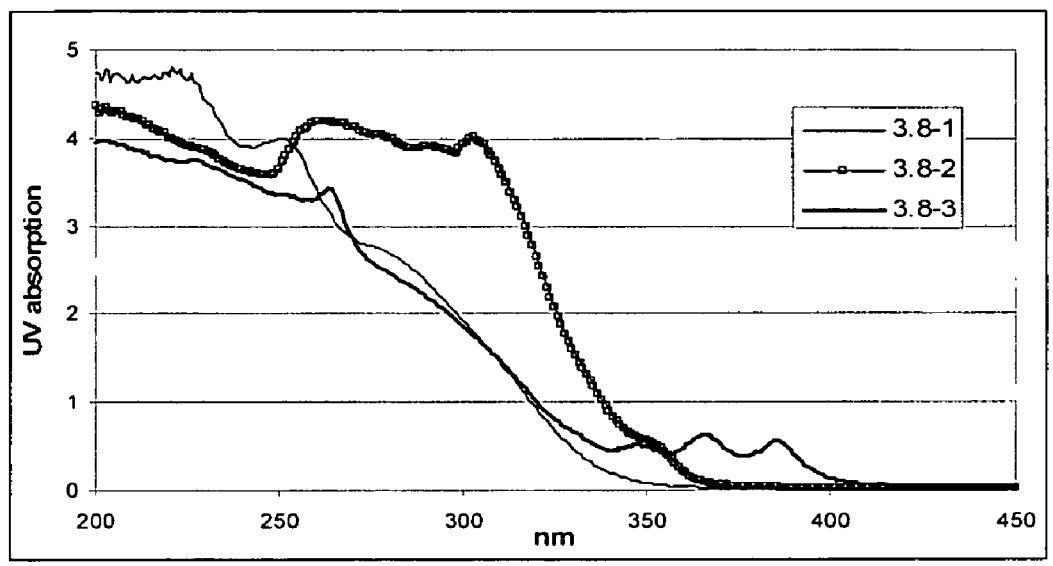
FIG. 6 is a graph showing the UV absorption spectra of coatings produced with various coating formulations in accordance with the present invention.

Third, the via's inner and outer diameter are larger. Since the laser beam's spiral diameter is 200 μm, a sample having an outer diameter closer to 200 μm is considered to be a better ablated one. After 4 pulses ablation on the 3.8 and 3.10 samples, such improvement is pronounced especially for samples with ACA-OL, for which the diameter is double that of the blank sample. When the films were ablated by more pulses, the difference between sensitized samples and original ones is less pronounced since the sensitizer's effect is overwhelmed by high laser energy input. Coatings sensitized by ACA-OL were found to have better performance in laser ablation at 355 nm. This can be explained by their broader and stronger absorption at around 355 nm. The UV absorption spectra for coating films containing the different sensitizers are shown in FIG. 6.

Figure 7:
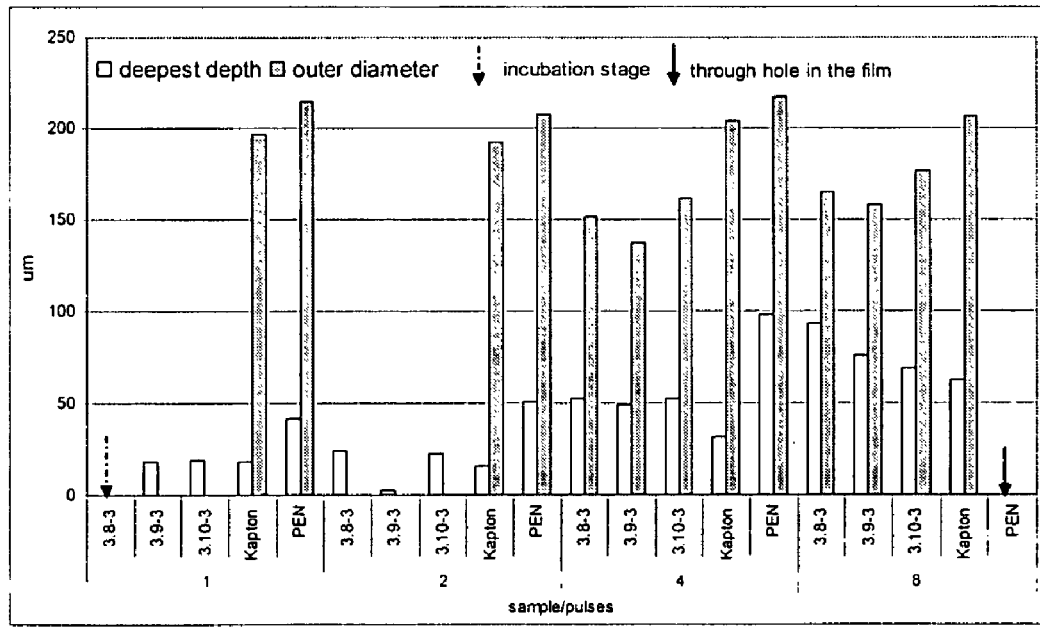
FIG. 7 is a bar graph showing the depth and diameter of vias created by laser ablation of coatings produced with various coating formulations in accordance with the present invention and of two reference coating materials, Kapton and PEN.

Comparison of sensitized coatings with Kapton and PEN for laser ablation: Two reference materials, Kapton (polyimide) and poly(ethylene naphthalene) ("PEN") were chosen as references in the laser ablation experiments. These reference materials were ablated under the same conditions as the sample films. Film thickness for the Kapton reference material was 75 μm, and film thickness for the PEN reference material was 125 μm. Kapton is considered a standard commercial material for laser ablation, which ablation is mainly based on thermal mechanism (Ortelli; and Lippert I, which are hereby incorporated by reference). PEN is expected to have good ablation performance due to a high content of naphthalene moieties in the polymer backbone. ACA-OL sensitized coating samples were used to compare with Kapton and PEN because of their better ablation performance. The comparison results are shown in FIG. 7. Considering Kapton via's unique profile, only the vias' deepest depth and outer diameter were compared. Note that the coating samples' outer diameter were measured only at 4 and 8 pulses). From FIG. 7 it can be seen that PEN's ablation performance is much better than the other materials (much deeper depth and larger diameter), and a through hole was drilled even at 8 pulses. ACA-OL sensitized coating samples' have better ablation depth than Kapton. As to the outer diameter, Kapton and PEN's vias reach about 200 μm outer diameter immediately after the first pulse; in contrast, the outer diameters of the coating samples' vias are much smaller than 200 μm even after 8 pulses. The coating samples thus seem to be less efficient in utilizing the laser beam's surrounding energy, relative to Kapton and PEN.

Example 7

Results Regarding the Synthesis and Characterization and Effects of Reactive Sensitizers—Effect of Tg on Laser Ablation Tg is one of a polymer's key properties and is related to many polymer behaviors. It was found that polymers with crosslinked structure or with higher molecular weight are more difficult to ablate, probably due to their higher stability and viscosity (Lippert I, which is hereby incorporated by reference). No report on the relationship between polymer's Tg and laser ablation behavior has been found. We designed a series of samples, as shown in Tables 3A-3C (3.8-4, 3.8-5 and 3.10-4, 3.10-5), with Tg variation in order to study the effect of Tg on laser ablation. In the 3.8 and 3.10 systems, Tg was varied by changing the percentage of difunctional monomers (DOX or ECC respectively) present. NDC-OX was added to the 3.8 system in order to further examine reactive sensitizer's effect. The basic thermal and mechanical properties of these formulations were tested, and the results are shown in Table 7.

TABLE 7

| | 3.8-1 | 3.8-4 | 3.8-41 | 3.8-5 | 3.8-51 | 3.10-1 | 3.10-4 | 3.10-5 |
|---|---|---|---|---|---|---|---|---|
| Film Thickness (μm) | 90 | 110 | 80 | 90 | 90 | 90 | 110 | 110 |
| X-hatch adhesion | | | 25/25 | | | | 25/25 | |
| Curling* | sl. | med. | med. | ser. | ser. | v.sl. | med. | med. |
| DSCTg(°C.) | 49.98 | 51.26 | 50.01 | 51.42 | 51.73 | 45.36 | 48.57 | 50.46 |
| DMTATg 1 (°C.) | 135.5 | 142.4 | 145.2 | 145.4 | 154.9 | 93.59 | 125.7 | 140.4 |
| DMTA Tg 2 (°C.) | | | not observed | | | 132.5 | 173.9 | no |
| $v_e$ (× mmol/cm³) | 8.203 | 11.36 | 15.74 | 20.99 | 17.36 | 2.420 | 3.542 | 5.012 |

*v.sl. = very slight; sl. = slight; med. = medium; ser. = serious

Figure 8A:
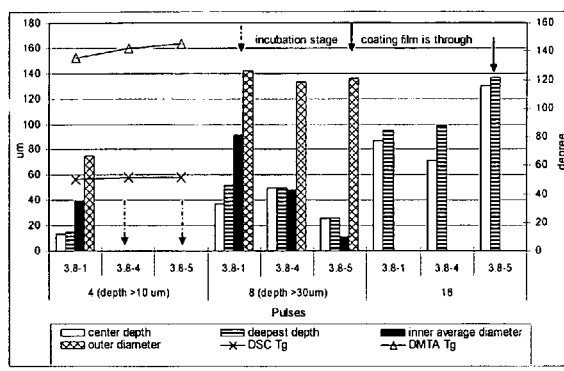
FIGS. 8A-8B are composite bar/line graphs showing the effect of Tg on the dimensions of vias formed by laser ablation of coatings produced with various coating formulations in accordance with the present invention.
Figure 8B:
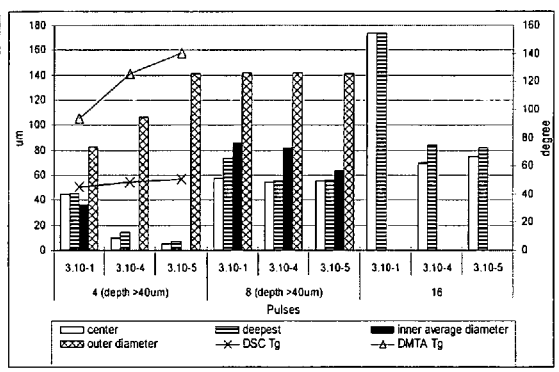
Figure 9A:
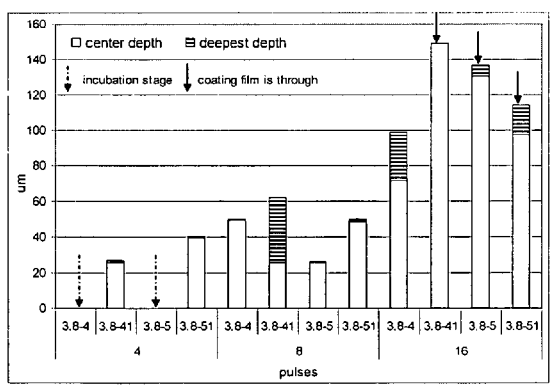
FIGS. 9A-9B are bar graphs showing the depth (FIG. 9A) and diameter (FIG. 9B) of vias created by laser ablation of coatings produced with various coating formulations in accordance with the present invention
Figure 9B:
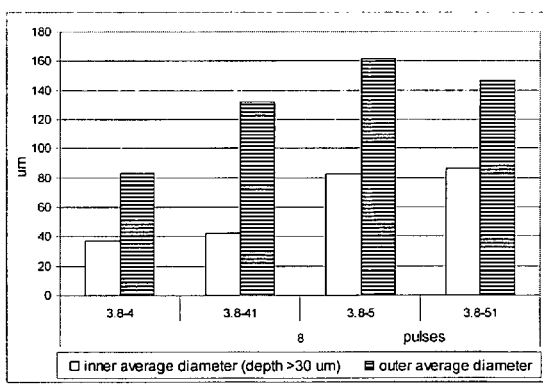

Referring to Table 7, it can be seen that, as the percentage of difunctional monomer increases, the coating's Tg and $v_e$ increase correspondingly. FIGS. 8A-8B show the relationship between Tg and laser ablation behavior of coating films. More particularly, FIGS. 8A-8B reveal that the higher the Tg (also higher $v_e$, since, here, the higher Tg is caused by denser network structure), the later the ablation starts, and the smaller the via dimension. This phenomena can be explained by more energy needed to break the network to liberate small molecules to create the via. Since thermal mechanism is inevitably involved in laser ablation process, it is likely that Tg, as one of polymer's most important thermal properties, will be a factor in the ablation process. The sensitizer's effect on higher Tg coating formulations were also examined, and the thermal and mechanical properties of these coating formulations are given in Table 7. RTIR and ablation results are shown in Table 8 and in FIGS. 9A-9B.

TABLE 8

| Time | Epoxide conversion (%) | | | | Oxetane conversion (%) | | | |
|---|---|---|---|---|---|---|---|---|
| (s) | 3.8-4 | 3.8-41 | 3.8-5 | 3.8-51 | 3.8-4 | 3.8-41 | 3.8-5 | 3.8-51 |
| 5 | 50 | 37 | 29 | 52 | 66 | 46 | 45 | 61 |
| 10 | 59 | 62 | 32 | 60 | 75 | 68 | 49 | 65 |
| 15 | 60 | 64 | 39 | 58 | 73 | 71 | 51 | 65 |
| 20 | 59 | 63 | 34 | 59 | 74 | 74 | 50 | 68 |
| 25 | 59 | 69 | 39 | 63 | 76 | 77 | 51 | 70 |
| 30 | 63 | 71 | 44 | 62 | 76 | 76 | 54 | 71 |
| 60 | 60 | 71 | 44 | 65 | 79 | 80 | 60 | 73 |

TABLE 8-continued

| Time | Epoxide conversion (%) | | | | Oxetane conversion (%) | | | |
|---|---|---|---|---|---|---|---|---|
| (s) | 3.8-4 | 3.8-41 | 3.8-5 | 3.8-51 | 3.8-4 | 3.8-41 | 3.8-5 | 3.8-51 |
| 90 | 65 | 70 | 50 | 67 | 81 | 81 | 62 | 75 |
| 120 | 63 | 72 | 51 | 67 | 80 | 83 | 63 | 76 |

In coatings with higher Tg and $v_e$, such as 3.8-4 and 3.8-5, the addition of sensitizer still gives accelerated curing As a result, increased Tg and $v_e$ were observed in 3.8-41 compared to 3.8-4. But for 3.8-51, Tg and $v_e$ are lower than the blank formulation (3.8-5), indicating that, when the content of difunctional monomer is high enough, boosting such monomer's conversion may not further increase $v_e$ due to spatial factors. As to laser ablation performance, earlier start of ablation, deeper depth, and wider diameter of ablated vias were observed for sensitized coating films. These results further confirm the reactive sensitizer's role in aiding coating curing and laser ablation.

Example 8

Study of Cationic UV Curing and UV Laser Ablation Behavior of Coatings Sensitized by Novel Sensitizers—Results Summary Novel reactive sensitizers were synthesized by reacting naphthalene or anthracene derivatives with ECC, EHMO, and PCL. These sensitizers have good compatibility in cycloaliphatic epoxide based cationic UV curable coatings, and, consequently the coatings sensitized with about 1% wt sensitizers exhibit accelerated UV curing, resulting in higher Tg, hardness, and crosslink density. Profile and dimension data (depth and diameter) of vias created by YAG UV laser ablation on sensitized coating films and Kapton and PEN reference films were obtained. Larger depth and diameter were found for sensitized coatings than non sensitized ones. ACA-OL sensitized coatings have best laser ablation performance among the tested coating samples. This result can be explained by anthracene's stronger and broader absorption around 355 nm. These coatings even have greater laser ablation depths and diameters than Kapton, which is widely accepted as a standard laser ablation material. Moreover, the reactive sensitizers did not exhibit any adverse effect on coating performance. The effect of Tg on laser ablation behavior was investigated, and it was found that laser ablation becomes more difficult with higher Tg and $v_e$.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention, as defined in the claims which follow.

What is claimed is:

1. A compound having the formula:

Q-L-Z where Q- represents a fused aromatic moiety; -L- represents a linking moiety comprising a carboxylate ester; and -Z represents a moiety containing an oxetane or oxirane ring.

2. A compound according to claim 1, wherein Q- represents a fused aromatic moiety selected from the group consisting of a naphthalene moiety, an anthracene moiety, and a pyrene moiety.

3. A compound according to claim 1, wherein Q- represents a substituted fused aromatic moiety having the formula:

Z'-L'-Q'- wherein -Q'- represents a fused aromatic moiety; -L'- represents a linking moiety; and Z'- represents a moiety containing an oxetane or oxirane ring.

4. A compound according to claim 1, wherein the compound has the formula:

Z'-L'-Q'-L-Z where -Q'- represents a fused aromatic moiety; -L'- represents a linking moiety; and Z'- represents a moiety containing an oxetane or oxirane ring.

5. A compound according to claim 1, wherein Z has the formula:

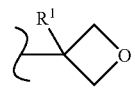

wherein $R^1$ represents a hydrogen atom or a substituted or unsubstituted alkyl group.

6. A compound according to claim 5, wherein $R^1$ represents an ethyl group.

7. A compound according to claim 1, wherein Z has the formula:

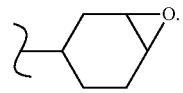

8. A compound according to claim 1, wherein L represents a moiety having the formula:

—C(O)—O—$R^2$ where $R^2$ is an alkylene group.

9. A compound according to claim 8, wherein $R^2$ is a methylene group.

10. A compound according to claim 1, wherein L represents a moiety having the formula:

—C(O)—O—$R^4$—C(O)—O—$R^3$— where $R^3$ and $R^4$ independently represent the same or different alkylene groups.

11. A compound according to claim 10, wherein $R^3$ is a linear alkylene group and $R^4$ is a cyclic alkylene group.

12. A compound according to claim 11, wherein $R^3$ is a methylene group and $R^4$ is a cyclohex-1,4-diyl group.

13. A compound according to claim 11, wherein L represents a moiety having the formula:

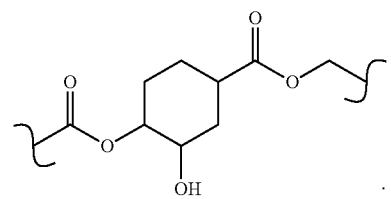

14. A compound according to claim 1, wherein said compound has the formula:

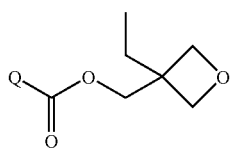

and wherein Q- represents a fused aromatic moiety.

15. A compound according to claim 14, wherein said compound has the formula:

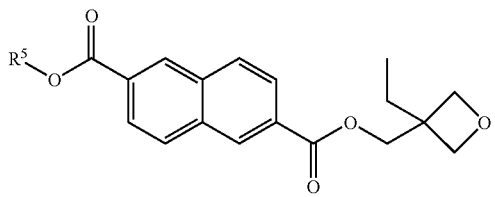

and wherein $R^5$ represents a substituted or unsubstituted alkyl group.

16. A compound according to claim 15 wherein $R^5$ represents a methyl group.

17. A compound according to claim 1, wherein said compound has the formula:

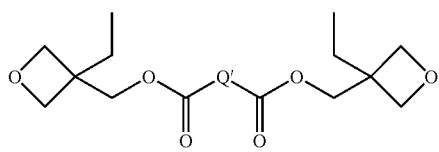

and wherein -Q'- represents a fused aromatic moiety.

18. A compound according to claim 17, wherein said compound has the formula:

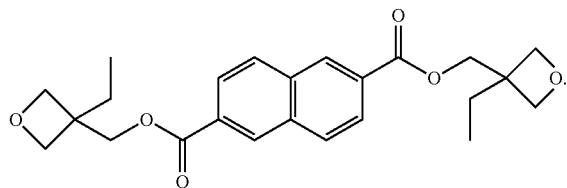

19. A compound according to claim 1, wherein said compound has the formula:

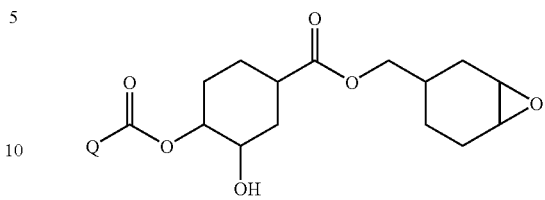

and where Q- represents a fused aromatic moiety.

20. A compound according to claim 19, wherein said compound has the formula:

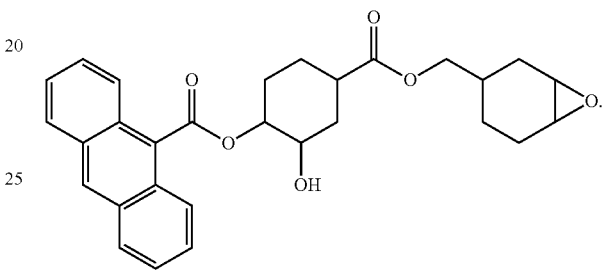

21. A method for making a compound according to claim 1, said method comprising:
providing an ester having the formula Q-COOR$^6$, wherein R$^6$ is a substituted or unsubstituted alkyl group;
providing an alcohol having the formula HO-Z; and
contacting the ester having the formula Q-COOR$^6$ with the alcohol having the formula HO-Z under conditions effective to effect transesterification;
wherein Q- represents a fused aromatic moiety; and -Z represents a moiety containing an oxetane or oxirane ring.

* * * * *